(12) United States Patent
Adib et al.

(10) Patent No.: US 10,746,852 B2
(45) Date of Patent: Aug. 18, 2020

(54) VITAL SIGNS MONITORING VIA RADIO REFLECTIONS

(71) Applicant: Massachusetts Institute of Technology, Cambridge, MA (US)

(72) Inventors: Fadel Adib, Cambridge, MA (US); Zachary Edward Kabelac, Somerville, MA (US); Dina Katabi, Cambridge, MA (US)

(73) Assignee: Massachusetts Institute of Technology, Cambridge, MA (US)

(*) Notice: Subject to any disclaimer, the term of this patent is extended or adjusted under 35 U.S.C. 154(b) by 565 days.

(21) Appl. No.: 15/307,607

(22) PCT Filed: Apr. 28, 2015

(86) PCT No.: PCT/US2015/027945
§ 371 (c)(1),
(2) Date: Oct. 28, 2016

(87) PCT Pub. No.: WO2015/168093
PCT Pub. Date: Nov. 5, 2015

(65) Prior Publication Data
US 2017/0042432 A1 Feb. 16, 2017

Related U.S. Application Data

(60) Provisional application No. 62/117,087, filed on Feb. 17, 2015, provisional application No. 61/985,066, filed on Apr. 28, 2014.

(51) Int. Cl.
*G01S 7/41* (2006.01)
*A61B 5/113* (2006.01)
(Continued)

(52) U.S. Cl.
CPC ............ *G01S 7/415* (2013.01); *A61B 5/0255* (2013.01); *A61B 5/08* (2013.01); *A61B 5/113* (2013.01); *G01S 13/536* (2013.01)

(58) Field of Classification Search
CPC . A61B 5/024–0255; A61B 5/113; A61B 5/08; G01S 13/522; G01S 7/415; G01S 13/50–64
See application file for complete search history.

(56) References Cited

U.S. PATENT DOCUMENTS 7,811,234 B2 * 10/2010 McGrath ................ A61B 5/024
600/508
7,916,066 B1 3/2011 Osterweil
(Continued)

FOREIGN PATENT DOCUMENTS

CN 1342968 A 4/2002
EP 2492709 8/2012
(Continued)

OTHER PUBLICATIONS

Anitori, Laura et al.; "FMCW radar for life-sign detection," In 2009 IEEE Radar Conference, pp. 1-6, IEEE (2009).
(Continued)

*Primary Examiner* — Matthew M Barker
(74) *Attorney, Agent, or Firm* — Occhiuti & Rohlicek LLP

(57) ABSTRACT

A method for monitoring periodic motions of one or more subjects uses signal reflections from the subjects. The method includes emitting a transmitted signal from a transmitting antenna and receiving a received signal at one or more receiving antennas. The received signal includes a combination of a number of reflections of the transmitted signal, at least some of which are associated with the subjects. The received signal, including the reflections, is
(Continued)

processed to determine an estimate of a fundamental frequency of the periodic motions.

42 Claims, 10 Drawing Sheets

(51) Int. Cl.
*A61B 5/08* (2006.01)
*G01S 13/536* (2006.01)
*A61B 5/0255* (2006.01)

(56) References Cited

U.S. PATENT DOCUMENTS

| | | | | |
|---|---|---|---|---|
| 8,232,866 | B2* | 7/2012 | McGrath | G07C 9/00158 |
| | | | | 340/5.1 |
| 8,721,554 | B2* | 5/2014 | Lin | A61B 5/05 |
| | | | | 600/484 |
| 9,186,079 | B2* | 11/2015 | Mase | A61B 5/021 |
| 9,229,102 | B1* | 1/2016 | Wright | G01S 13/888 |
| 9,443,419 | B2* | 9/2016 | Wilson | A61B 5/6889 |
| 9,477,812 | B2* | 10/2016 | Lin | A61B 5/05 |
| 9,492,099 | B2* | 11/2016 | Gamble | A61B 5/0507 |
| 2003/0209077 | A1 | 11/2003 | Battenberg et al. | |
| 2008/0077015 | A1* | 3/2008 | Boric-Lubecke | A61B 5/0205 |
| | | | | 600/453 |
| 2008/0074307 | A1 | 5/2008 | Boric-Lubecke et al. | |
| 2008/0119716 | A1* | 5/2008 | Boric-Lubecke | A61B 5/0205 |
| | | | | 600/407 |
| 2008/0234568 | A1* | 9/2008 | Ouchi | A61B 5/024 |
| | | | | 600/407 |
| 2008/0275328 | A1* | 11/2008 | Jones | A61B 5/024 |
| | | | | 600/407 |
| 2008/0275337 | A1* | 11/2008 | Fossan | A61B 5/0507 |
| | | | | 600/428 |
| 2008/0316085 | A1 | 12/2008 | Rofougaran et al. | |
| 2009/0209850 | A1* | 8/2009 | Tao | A61B 5/024 |
| | | | | 600/425 |
| 2009/0278728 | A1 | 11/2009 | Morgan et al. | |
| 2009/0303108 | A1 | 12/2009 | Hilsebecher et al. | |
| 2010/0241009 | A1* | 9/2010 | Petkie | A61B 5/024 |
| | | | | 600/484 |
| 2012/0116187 | A1 | 5/2012 | Hayes et al. | |
| 2012/0192617 | A1 | 8/2012 | Walton et al. | |
| 2012/0274498 | A1 | 11/2012 | Hyde et al. | |
| 2013/0113647 | A1* | 5/2013 | Sentelle | G01S 13/32 |
| | | | | 342/22 |
| 2013/0300573 | A1* | 11/2013 | Brown | A61B 5/1113 |
| | | | | 340/870.01 |
| 2014/0058256 | A1* | 2/2014 | De Jong | A61B 5/02411 |
| | | | | 600/430 |
| 2015/0164379 | A1* | 6/2015 | Lin | A61B 5/113 |
| | | | | 600/301 |
| 2015/0301167 | A1* | 10/2015 | Sentelle | A61B 5/0205 |
| | | | | 342/22 |
| 2016/0022204 | A1* | 1/2016 | Mostov | A61B 5/0002 |
| | | | | 600/301 |
| 2016/0030006 | A1* | 2/2016 | Okuya | G01S 13/56 |
| | | | | 702/150 |
| 2016/0200276 | A1* | 7/2016 | Diewald | G01S 7/354 |
| | | | | 342/28 |
| 2016/0311388 | A1* | 10/2016 | Diewald | G01S 13/04 |
| 2017/0150891 | A1* | 6/2017 | Tsuchimoto | A61B 5/02 |
| 2017/0300650 | A1* | 10/2017 | Margon | A61B 5/024 |
| 2018/0054262 | A1* | 2/2018 | Noethlings | H03D 3/008 |

FOREIGN PATENT DOCUMENTS

| | | | | |
|---|---|---|---|---|
| GB | 2349759 A | * 11/2000 | | A61B 5/021 |
| WO | 2009/047546 | 4/2009 | | |
| WO | 2013/177431 | 11/2013 | | |

OTHER PUBLICATIONS

Nguyen, Van et al., "Harmonic Path (HAPA) algorithm for non-contact vital signs monitoring with IR-UWB radar." In 2013 IEEE Biomedical Circuits and Systems Conference (BioCAS), pp. 146-149 IEEE (2013).

Wang, Yazhou et al.; "Simultaneous Localization and Respiration Detection of Multiple People Using Low Cost UWB Biometric Pulse Doppler Radar Sensor," IEEE, 978-1-4673-1088 (2012).

Zhang, Dan et al.; "FMCW Radar for Small Displacement Detection of Vital Signal Using Projection Matrix Method," International Journal of Antennas and Propagation, vol. 2013, Article ID 571986, 5 pages (2013).

* cited by examiner

VITAL SIGNS MONITORING VIA RADIO REFLECTIONS

CROSS-REFERENCE TO RELATED APPLICATIONS

This application is the National Stage of International Application No. PCT/US2015/027945, filed on Apr. 28, 2015 which claims the benefit of
U.S. Provisional Application No. 61/985,066 titled "MULTI-PERSON MOTION TRACKING VIA BODY RADIO REFLECTIONS," filed on Apr. 28, 2014, and
U.S. Provisional Application No. 62/117,087 titled "VITAL SIGNS MONITORING VIA RADIO REFLECTIONS," filed on Feb. 17, 2015.
This application is related to, but does not claim the benefit of:
U.S. Provisional Application No. 61/888,662 titled "MOTION TRACKING VIA BODY RADIO REFLECTIONS," filed on Oct. 9, 2013,
U.S. Provisional Application No. 61/943,957 titled "MULTI-PERSON MOTION TRACKING VIA BODY RADIO REFLECTIONS," filed on Feb. 24, 2014,
U.S. Utility application Ser. No. 14/510,263 titled "MOTION TRACKING VIA BODY RADIO REFLECTIONS," filed on Oct. 9, 2014.
These applications are incorporated herein by reference.

STATEMENT AS TO FEDERALLY SPONSORED RESEARCH

This invention was made with government support under CNS-1117194 awarded by the National Science Foundation. The government has certain rights in the invention.

BACKGROUND

This invention relates to monitoring vital signs, and more particularly to monitoring of breathing and/or heart rate via radio reflections.

The monitoring of vital signs (e.g., a human heart rate and breathing rate) of subjects without requiring that a monitoring device be in physical contact with the subjects is an active area of research. Contemporary approaches for non-contact vital signs monitoring can be divided into two areas: vision-based techniques and wireless techniques.

For vision based techniques, advances in image processing have allowed researchers to amplify visual patterns in video feeds (e.g., color changes due to blood flow) to detect breathing and heart rate. Such video-based techniques have drawbacks since they require the subject to face the camera and do not work properly when the subject turns away from the camera or is outside the camera's field of view.

For wireless techniques, advances in wireless transmission systems and signal processing have enabled researchers to monitor vital signs by analyzing characteristics of wireless signals that have reflected off of the subject. Some examples of wireless vital sign monitoring techniques utilize Doppler radar, WiFi, or ultra-wideband radar. One challenge in using wireless signals to monitor vital signs is that any motion in the environment affects the signal. Since breathing and heartbeats are minute movements, they can be easily masked by interference from any other source of movement in the environment. Furthermore, the presence of multiple users, even if the users are stationary, prevents systems from operating correctly since the wireless signal is affected by the combination of their vital signs, making it difficult to distinguish the vital signs of each individual. Conventional approaches deal with this problem by ensuring that there is only one source of motion in the environment: namely, the vital signs of the monitored individual. Hence, the experimental setups of the past approaches typically require a single person to lie still in close proximity to the device.

SUMMARY

Approaches described herein include mechanisms for separating different sources of motion in an environment. To do so, the approaches build on state-of-the-art wireless localization techniques that can identify the distance between the device and different moving objects. The approaches necessarily use these methods to distinguish the incoming signals based on distance, rather than estimating the actual location. By doing so, the approaches can distinguish signals reflected off of different bodies and body parts. The approaches then analyze the motion of the distinct signals independently to estimate the breathing and heart rate of one or more individuals.

In some embodiments, approaches described in the applications that are incorporated by reference are used to eliminate reflections from static objects (e.g., walls and furniture) and sort reflections from moving objects into bins (e.g., FFT samples representing ranges of TOF) based on their location relative to the device (i.e., based on the distance of the reflected path from transmitting to receiving antennas). Rather than or in addition to tracking power reflected from different distances to track the subtle motions associated with breathing and heartbeat, one or more embodiments use a model of wireless signals that captures both the reflected power and the phase of the signal.

In some embodiments, harmonic structure of periodic signals, for example, determined using phase-based processing, is used to determine vital signals, for instance, heart rate and/or breathing rate.

In an aspect, in general, a method for monitoring one or more periodic motions of one or more subjects using signal reflections from the subjects includes emitting a transmitted signal including repetitions of a transmitted signal pattern from a transmitting antenna, receiving, at one or more receiving antennas, a received signal including a combination of a number of reflections of the transmitted signal, at least some reflections of the number of reflections of the transmitted signal being associated with the one or more subjects, processing the received signal to form time successive patterns of the reflections of the transmitted signal from the one or more subjects, processing the time successive patterns of reflections to form one or more phase signals including, for each reflection of a subset of the number of reflections, forming a phase signal representing a variation over time of a phase angle for the reflection of the transmitted signal in the received signal, and processing each phase signal of a subset of the one or more phase signals to determine an estimate of a fundamental frequency of each periodic motion of the one or more periodic motions.

Aspects may include one or more of the following features.

Processing the received signal to form time successive patterns of the reflections of the transmitted signal from the one or more subjects may include forming the subset of the number of reflections including removing at least some extraneous reflections of the number of reflections according to reflection distance.

Forming the subset of the reflections may include, for each reflection of the number of reflections of the transmitted signal, determining whether the reflection is a static multipath reflection, excluding the reflection from the subset of the reflections if the reflection is a static multipath reflection, and including the reflection in the subset of the reflections if the reflection is not a static multipath reflection. Determining whether the reflection is a static multipath reflection may include using a time differencing approach.

The method may include determining the subset of the one or more phase signals including processing each of the one or more phase signals to determine a measure of periodicity of the phase signal and including the phase signal in the subset of the one or more phase signals if the measure of periodicity of the phase signal exceeds a predetermined threshold. Determining the estimate of the fundamental frequency of each periodic motion of the one or more periodic motions may include, for each periodic motion of the one or more periodic motions, determining a preliminary estimate of the fundamental frequency for the periodic motion and determining the estimate of the fundamental frequency for the periodic motion based on the preliminary estimate and a regression of the phase signal.

The one or more periodic motions may include periodic motions associated with one or more vital signs of a subject. The one or more periodic motions may include a periodic motion associated with heart beats of a subject. The one or more periodic motions may include a periodic motion associated with a subject breathing. The one or more periodic motions may include a periodic motion associated with an interfering movement of a subject. The one more periodic motions may include a periodic motion associated with a subject breathing and further includes a periodic motion associated with heart beats of the subject.

Processing each phase signal of the subset of the one or more phase signals to determine an estimate of a fundamental frequency of each periodic motion of the one or more periodic motions may include identifying a number of spectral peaks in a frequency domain representation of the phase signal, at least some of the spectral peaks being located at harmonic frequencies of the estimate of the fundamental frequency, and determining the estimate of the fundamental frequency from the identified one or more spectral peaks. Determining the estimate of the fundamental frequency from the identified one or more spectral peaks may include processing the one or more spectral peaks to determine a number of candidate fundamental frequencies for the periodic motion.

Processing the one or more spectral peaks to determine the number of candidate fundamental frequencies for the periodic motion may include, for each spectral peak, determining one or more factors of a frequency associated with the spectral peak that are in an expected frequency range of the fundamental frequency for the periodic motion, and including the determined one or more factors in the number of candidate fundamental frequencies for the periodic motion. The method may include processing the number of candidate fundamental frequencies to determine a preliminary estimate of the fundamental frequency for the periodic motion.

The method may include determining the estimate of the fundamental frequency based on the preliminary estimate of the fundamental frequency and a regression of the phase signal. The method may include filtering the phase signal to form a filtered version of the phase signal, including retaining frequency components at the preliminary estimate of the fundamental frequency and frequency components adjacent to the preliminary estimate of the fundamental frequency in the filtered version of the phase signal, and excluding substantially all other frequencies from the filtered version of the phase signal, and determining the estimate of the fundamental frequency of the periodic motion based on a regression of the filtered version of the phase signal.

Determining the estimate of the fundamental frequency of the periodic motion based on a regression of the filtered version of the phase signal may include determining a slope of a phase angle of the filtered version of the phase signal. Processing the number of candidate fundamental frequencies to determine the preliminary estimate of the fundamental frequency may include applying a voting algorithm to the number of candidate fundamental frequencies. Each phase signal of the subset of the one or more phase signals may include a first number of spectral peaks related to a periodic motion due to heart beats of the subject and a second number of spectral peaks related to a periodic motion due to the subject breathing.

Identifying the number of spectral peaks in the frequency domain representation of the phase signal may include applying a normalization algorithm to distinguish the spectral peaks from a noise floor of the frequency domain representation. Processing the phase signal of the subset of one or more phase signals to determine the estimate of the fundamental frequency of each periodic motion of the one or more periodic motions may include iteratively processing the phase signal. At least some of the subjects may be humans. The subset of the one or more phase signals may include a number of phase signals.

For each phase signal of the subset of the one or more phase signals, determining the estimate of the fundamental frequency for the periodic motion may include determining a preliminary estimate of the fundamental frequency of the periodic motion and determining the estimate of the fundamental frequency of the periodic motion based on the preliminary estimate of the fundamental frequency of the periodic motion and a regression of the phase signal. Determining the preliminary estimate of the fundamental frequency of the periodic motion may include identifying a frequency associated with a largest peak in a spectral representation of the phase signal and determining the estimate of the fundamental frequency of the periodic motion may include filtering the phase signal to form a filtered version of the phase signal, including retaining frequency components at the preliminary estimate and frequency components adjacent to the preliminary estimate in the filtered version of the phase signal, and excluding substantially all other frequencies from the filtered version of the phase signal. The estimate of the fundamental frequency of the periodic motion may be determined based on a regression of the filtered version of the phase signal. Determining the estimate of the fundamental frequency of the periodic motion based on a regression of the filtered version of the phase signal may include determining a slope of a phase angle of the filtered version of the phase signal.

One or more of the extraneous reflections may correspond to one or more objects in the environment. The one or more objects may be moving. The one or more objects may be periodically moving. The one or more objects may include a fan. The one or more objects may be static. The one or more objects may be vibrating. The vibration of the one or more objects may be periodic. Removing extraneous reflections of the number of reflections according to reflection distance may enable extraction of periodic movements of a number of subjects concurrently. Removing extraneous reflections of the number of reflections according to reflection distance may enable eliminating reflections form one or more different body parts of a human.

The one or more different body parts may include a limb. Removing extraneous reflections of the number of reflections according to reflection distance may enables eliminating reflections from one or more different objects on a human's body. The one or more different objects may include wearable objects including watches, cellular telephones, and jewelry. After being processed, the received signals from various human body parts may be combined to obtain an estimate of the fundamental frequencies of the one or more periodic motions with increased accuracy.

In another aspect, in general, a computer-implemented system for monitoring one or more periodic motions of one or more subjects using signal reflections from the subjects includes a processor programmed to perform some or all of the steps described above.

Aspects may include one or more of the following features.

The system may include a transmitter for emitting the transmitted signal and a receiver for receiving the received signal.

In another aspect, in general, software stored on a non-transitory computer-readable medium includes instructions for causing a processor to perform some or all of the steps of described above.

Aspects may include one or more of the following advantages.

Aspects allow for continuous monitoring of vital signs such as breathing and heart rate without requiring that subjects be in physical contact with a monitoring device. Since no device needs to be worn, elderly subjects are less likely to feel encumbered or ashamed by the monitoring device. Furthermore, some subjects (e.g., those with dementia) don't need to remember to put the device on. Children are unable to remove and misplace the device. Infants or those with sensitive skin won't develop skin irritation from the device.

Due to the non-invasive nature of the vital signs monitoring system, subjects can be continuously monitored (even while at home), allowing healthcare professionals to study how the subjects' vital signs correlate with their stress level and evolve with time and age.

Aspects monitor vital signs such as heart rate more accurately than certain conventional and comfortable technologies such as wristbands.

Aspects can simultaneously monitor the vital signs of multiple subjects.

Aspects can monitor the vital signs of subjects in the presence of extraneous motion.

Aspects do not require subjects to lie still on a bed facing the device.

Aspects can track subjects' breathing and heart rates with a median accuracy of 99%, even when users are 8 meters away from the device, or in a different room.

Aspects have a median accuracy for breathing of 99.3% and for heart rate of 98.5% when a subject is 1 m away from the device. Aspects have a median accuracy for breathing 98.7% and for heart rate of 98.3% when the subject is 8 m away from the device.

Other features and advantages of the invention are apparent from the following description, and from the claims.

DESCRIPTION

1 System Overview

Figure 1:
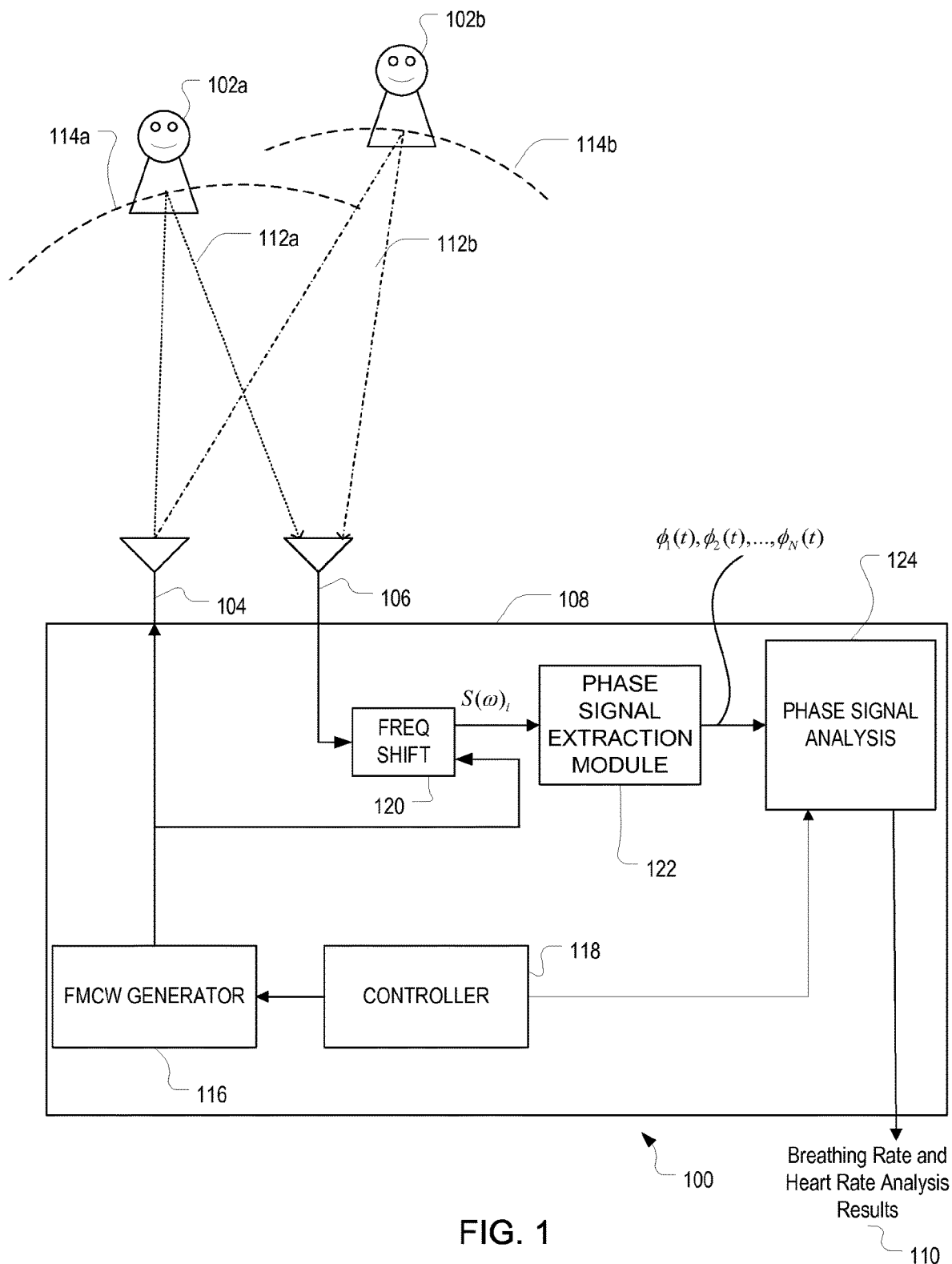
FIG. 1 is a schematic block diagram of an embodiment of a vital signs monitoring system.

Referring to FIG. 1, a vital signs monitoring system 100 monitors the vital signs (e.g., breathing rate and heart rate) of one or more subjects 102a, 102b without requiring any physical contact between the one or more subjects and the vital signs monitoring system 100. The vital signs monitoring system 100 includes a transmitting antenna 104, a receiving antenna 106, and a signal processing subsystem 108. Note that, in some examples, rather than having a single receiving antenna and a single transmitting antenna, the system 100 includes a plurality of receiving antennas and/or a plurality of receiving antennas. However, for the sake of simplifying the description of the vital signs monitoring system, the following description refers only to a single receiving/single transmitting antenna embodiment.

In general, the vital signs monitoring system 100 transmits a low power wireless signal into an environment surrounding the system 100 from the transmitting antenna 104. The transmitted signal reflects off of the one or more subjects 102a, 102b (among other objects such as walls and furniture in the environment) and is then received by the receiving antenna 106. The received reflected signal is processed by the signal processing subsystem 108 to determine breathing rate and heart rate analysis results 110 for the one or more subjects 102a, 102b.

The system 100 exploits the fact that characteristics of wireless signals are affected by motion in the environment, including chest movements due to inhaling and exhaling and skin vibrations due to heartbeats. In particular, as the subjects breathe and as their hearts beat, a distance between the antennas of the system 100 and the subjects 102a, 102b (e.g., the chests of the subjects) varies. In some examples, the system 100 monitors the distance between the antennas of the system and the subjects 102a, 102b using time-of-flight (TOF) (also referred to as "round-trip time") information derived for the transmitting and receiving antennas 104, 106.

For example, in FIG. 1, two paths 112a and 112b between the transmitting antenna 104 and the receiving antenna 106 are shown reflecting off of two representative subjects 102a and 102b, respectively. Assuming a constant signal propagation speed c (i.e., the speed of light), the TOF from a transmitting antenna at coordinates $(x_t, y_t, z_t)$ reflecting from an subject at coordinates $(x_o, y_o, z_o)$ and received at a receiving antenna at coordinates $(x_r, y_r, z_r)$ can be expressed as $$\frac{1}{c}\left(\begin{array}{l}\sqrt{(x_t - x_o)^2 + (y_t - y_o)^2 + (z_t - z_o)^2} + \\ \sqrt{(x_r - x_o)^2 + (y_r - y_o)^2 + (z_r - z_o)^2}\end{array}\right)$$

In this case, with a single pair of antennas, the TOF associated with each of the paths 112a, 112b constrains the location of the respective subject to lie on an ellipsoid defined by the three-dimensional coordinates of the transmitting and receiving antennas of the path, and the path distance determined from the TOF. For illustration, a portion of the ellipsoid for each of the paths 112a, 112b is depicted using elliptical lines 114a, 114b.

As is described in greater detail below, any movement associated with two different subjects that lie on different ellipsoids (i.e., two subjects that are at different distances from the antennas) can be isolated and analyzed separately.

As is noted above, for each of the subjects 102a, 102b, the distance of the ellipsoid from the pair of transmitting and receiving antennas varies with to the subject's chest movements due to inhaling and exhaling and skin vibrations due to heartbeats. The varying distance between the antennas 104, 106 and the subject is manifested in the reflected signal as a phase variation in a signal derived from the transmitted and reflected signals over time. Generally, the vital signs monitoring system 100 extracts a signal representative of this phase variation from the transmitted and reflected signals and processes the phase variation signal to determine the vital signs of the one or more subjects.

2 Sin Processing Subsystem

The signal processing subsystem 108 includes a signal generator 116, a controller 118, a frequency shifting module 120, a phase signal extraction module 122, and a phase signal analysis module 124.

The controller 118 controls the signal generator 116 to generate repetitions of a signal pattern that is emitted from the transmitting antenna 104. In the embodiment of FIG. 1, the signal generator 116 is an ultra wide band frequency modulated carrier wave (FMCW) generator 116. It should be understood that in other embodiments other signal patterns and bandwidth than those described below may be used while following other aspects of the described embodiments.

The repetitions of the signal pattern emitted from the transmitting antenna 104 reflect off of the subjects 102a, 102b and other objects in the environment, and are received at the receiving antenna 106. The reflected signal received by receiving antenna 106 is provided to the frequency shifting module 120 along with the transmitted signal generated by the FMCW generator 116. The frequency shifting module 120 frequency shifts (e.g., "downconverts" or "downmixes") the received signal according to the transmitted signal (e.g., by multiplying the signals) and transforms the frequency shifted received signal to a frequency domain representation (e.g., via a Fast Fourier Transform (FFT)) resulting in a frequency domain representation of the frequency shifted received signal, $S(\omega)_i$ at a discrete set of frequencies, $\omega$.

The frequency domain representation of the frequency shifted signal, $S(\omega)_i$ is provided to the phase signal extraction module 122 which processes $S(\omega)_i$ to extract N phase signals, $\phi_1(t), \phi_2(t), \ldots, \phi_N(t)$. See, for example, the N=2 outputs, $\phi_A(t), \phi_B(t)$ shown in FIG. 4. In some examples, each of the one or more phase signals, $\phi_1(t), \phi_2(t), \ldots, \phi_N(t)$, corresponds to one of the ellipsoids in the environment where the phase extraction module 122 has detected motion (e.g., the motion of the chest of one of the subjects).

The one or more phase signals, $\phi_1(t), \phi_2(t), \ldots, \phi_N(t)$, are provided to the phase signal analysis module 124 which processes each of the one or more phase signals, $\phi_1(t), \phi_2(t), \ldots, \phi_N(t)$, to determine the breathing rate and heart rate analysis results 110.

2.1 Frequency Shifting

Figure 2A:
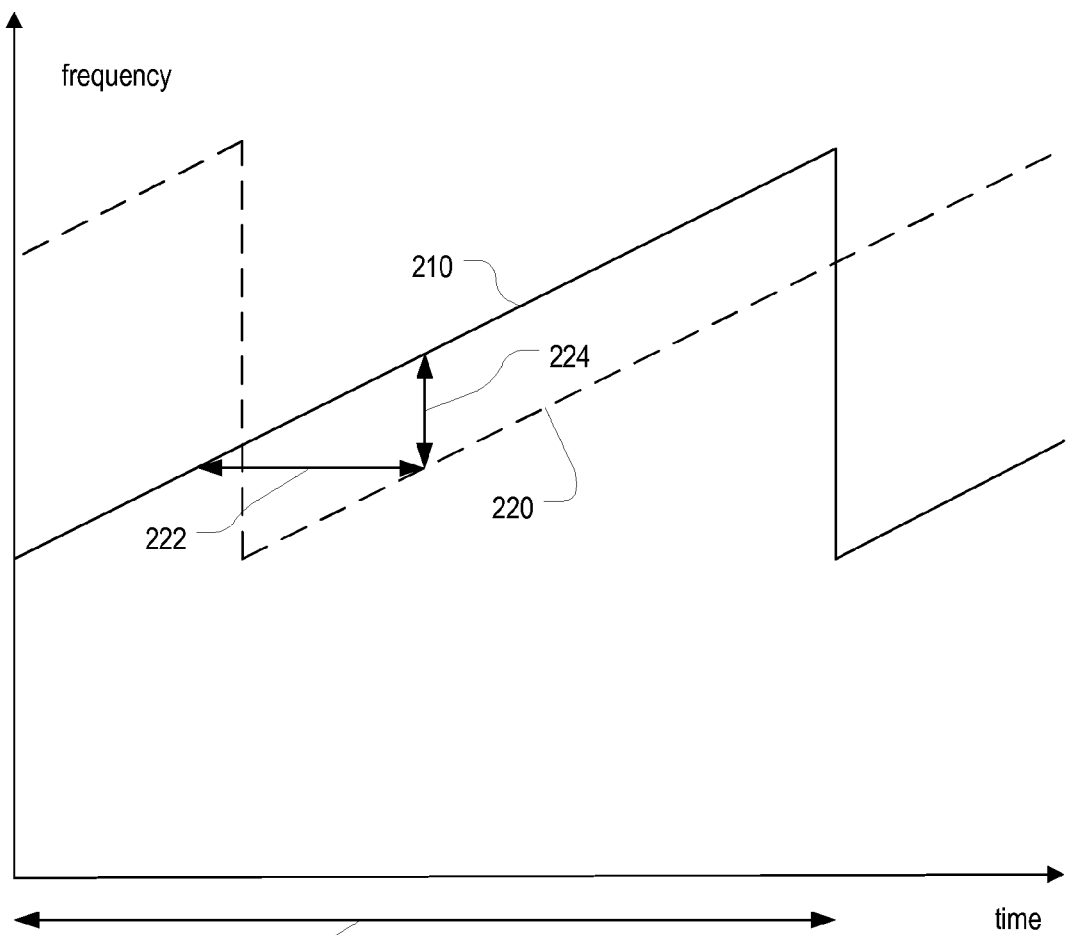
FIG. 2A is a plot of transmit and receive frequency over time.

Referring to FIG. 2A, a transmit signal received by the frequency shifting module 120 includes a series of repeating time intervals 212 of duration 1T. For each of the time intervals, a transmit frequency is swept over a frequency range as shown by solid line 210. In some embodiments, the frequency range is 5.46-7.25 GHz (i.e., a frequency range of approximately 1.8 GHz) with a sweep duration and repetition rate of 2.5 milliseconds. The receive signal that the frequency shifting module 120 receives from the receiving antenna 106 is a version of the transmit signal that is delayed by the TOF 222 of the signal (i.e., when reflected from a single object) and has a frequency as shown in the dashed line 220. Note that the TOF 222 corresponds to a difference 224 in transmitted and received frequencies, which is a product of the TOF and the rate of frequency change of the swept carrier for the transmitting antenna.

Figure 2B:
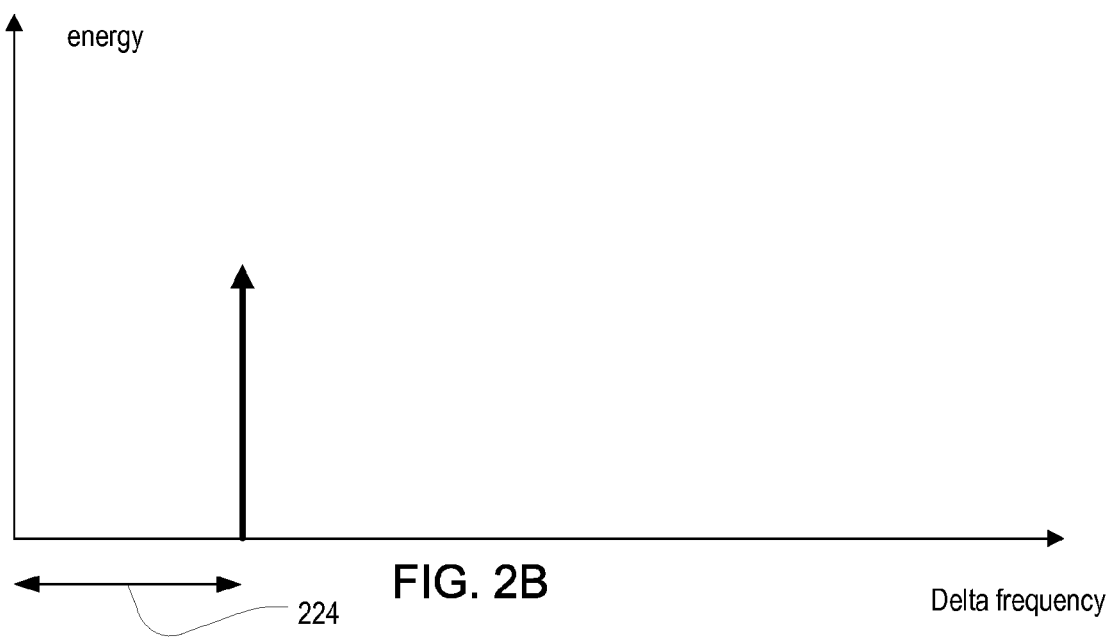
FIG. 2B is a plot received energy over frequency corresponding to FIG. 2A.

Referring to FIG. 2B, if the received reflected signal (dashed line 220 in FIG. 2A) is frequency shifted according to transmitted signal (solid line 210 in FIG. 2A) then the result will have energy concentrated at the frequency difference 224 corresponding to the TOF. (Note that we are ignoring the edges of the intervals 212, which are exaggerated in the figures). The frequency shifting module 120 of FIG. 1 (also referred to as a "downconverter" or a "mixer") implements the frequency shifting, for example, including a modulator that modulates the received signal with the transmitted signal and retaining a low frequency range representing TOF durations that are consistent with the physical dimensions of the environment.

The output of the frequency shifter is subject to a spectral analysis (e.g., a Fourier Transform) to separate the frequency components each associated with a different TOF. In this embodiment, the output of the frequency shifter is sampled and a discrete time Fourier Transform implemented as a Fast Fourier Transform (FFT) is computed for each interval 212. Each complex value of the FFT provides a frequency sample with a frequency resolution $\Delta f = 1/T_{sweep}$ where $T_{sweep}$ is the sweep duration (e.g., 2.5 milliseconds).

Continuing to refer to FIG. 2B, it should be recognized that the distribution of energy over frequency (and equivalently over TOF), is not generally concentrated as shown in the diagram. Rather, there is a distribution of energy resulting from the superposition of reflections from the reflective objects in the environment.

2.2 Phase Signal Extraction

Figure 3:
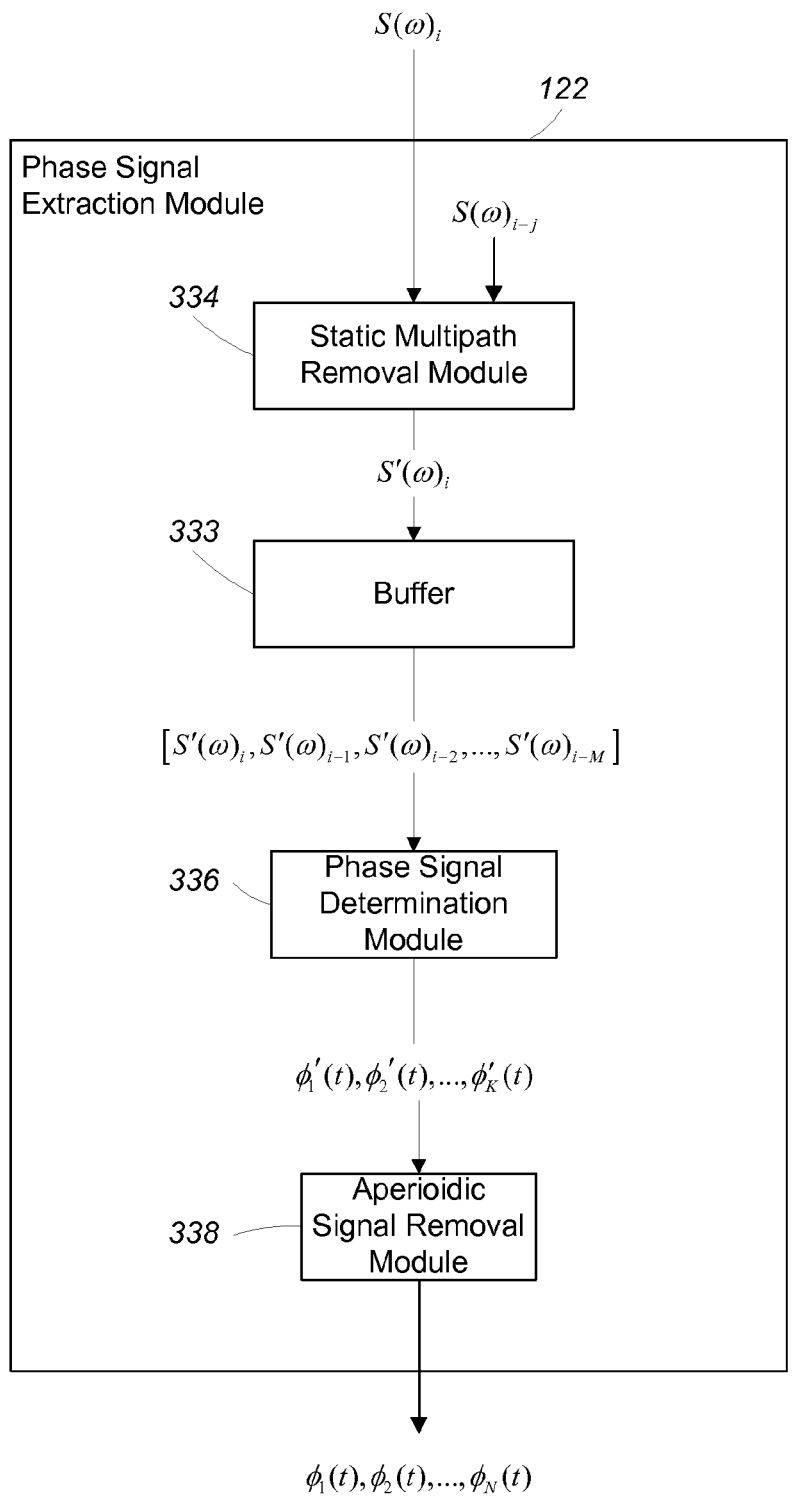
FIG. 3 is a schematic block diagram of an embodiment of a phase signal extraction module.

Referring to FIG. 3, the FFT output for each time interval, $S(\omega)_i$ is provided to the phase signal extraction module 122. The phase signal extraction module 122 processes each FFT output, $S(\omega)_i$ to extract N phase signals, $\phi_1(t), \phi_2(t), \ldots,$ $\phi_N(t)$, each corresponding to movement in the environment of the system 100 due to the breathing and heart beats of the subjects 102a, 102b.

In general, each FFT output, $S(\omega)_i$ received by the phase signal extraction module 122 includes one or more areas of concentrated energy. Each individual area of concentrated energy is sometimes referred to as a 'reflection' since corresponds to a reflection in the signal received at the receiving antenna 106. Some reflections are direct, with the path being direct between the reflecting object and the transmitting and receiving antennas. Other reflections exhibit multipath effects in which there are multiple paths from a transmitting antenna to a receiving antenna via a particular reflecting object. Some multipath effects are due to the transmitted signal being reflected off wall, furniture, and other static objects in the environment. These types of multipath effects are referred to as static multipath effects.

The phase signal extraction module 122 includes a static multipath removal module 334, a buffer 333, a phase signal determination module 336, and an aperiodic signal removal module 338.

2.2.1 Static Multipath Removal

In some examples, the FFT output, $S(\omega)_i$ is first provided to the static multipath removal module 334 along with one or more previously received values 335 of the FFT output (e.g., a value of $S(\omega)$ that was received j time intervals, or sweeps, ago: $S(\omega)_{i-j}$). The static multipath removal module 334 processes $S(\omega)_i$ and the one or more previously received values 335 of $S(\omega)_i$ to remove static multipath effects using a time differencing approach. The time differencing approach used by the static multipath removal module 334 distinguishes a moving object's reflections from reflections off static objects in the environment, like furniture and walls. In particular, reflections from walls and furniture are much stronger than reflections from a human, especially if the human is behind a wall. Unless these reflections are removed, they would mask the signal coming from the human and prevent sensing her motion. This behavior is called the "Flash Effect'".

To remove reflections from the static objects (walls, furniture), the static multipath removal module 334 leverages the fact that since these reflectors are static, their distance to the antenna array does not change over time, and therefore their induced frequency shift stays constant over time. For each sweep window, $S(cu)$ the static multipath removal module 334 eliminates the power from the static reflectors by subtracting the (complex) output of $S(\omega)_i$ in the given sweep from the output of one or more previous sweeps (e.g., $S(\omega)_{i-j}$). This process is called background subtraction because it eliminates all the static reflectors in the background. In some embodiments, j=1 and the FFT output from the immediately previous sweep, $S(\omega)_{i-1}$ is subtracted from the current FFT output $S(\omega)_i$. In other examples, j is selected such that a previous FFT output is selected using a small time delay (i.e., 2.5 milliseconds previous), while in other embodiments, a greater time delay may be used (e.g., 12.5 milliseconds, or even over a second, such as 2.5 seconds).

The result of the background subtraction process performed by the static multipath removal module 334 is a static multipath free FFT output, $S'(\omega)_i$ which includes substantially only reflections corresponding to moving objects in the environment.

2.2.2 Phase Signal Extraction

The static multipath free FFT output, $S'(\omega)_i$ is then provided to the buffer 333 which stores a number (i.e., M) of previous static multipath free FFT outputs, $S'(\omega)_i$, $S'(\omega)_{i-1}$, $S'(\omega)_{i-2}$, ..., $S'(\omega)_{i-M}$. In some examples, the value of M is chosen such that the buffer 333 represents a predetermined amount of time (e.g., 30 seconds) of the signal received by the receiving antenna 106. In some examples, the buffer 333 is a first-in-first-out (FIFO) buffer that, upon receiving a new result, $S'(\omega)_i$, pushes the new result $S'(\omega)_i$ into the head of the buffer 333 and evicts an oldest result, $S'(w)_{i-M}$ from the end of the buffer 333.

The M static multipath free FFT outputs, $S'(\omega)_i$, $S'(\omega)_{i-1}$, $S'(\omega)_{i-2}$, ..., $S'(\omega)_{i-M}$ in the buffer 333 are provided to the phase signal determination module 336 that identifies K reflections that are present in (substantially all of) the M static multipath free FFT outputs. See, for example, the K=3 reflections A, B, and C in FIG. 4. The phase signal determination module 336 then extracts a "phase signal," $\phi_k'(t)$ for each of the identified reflections.

In general, each of the K identified reflections is located in the same FFT bin in all of the M static multipath free FFT outputs, $S'(\omega)_i$, $S'(\omega)_{i-1}$, $S'(\omega)_{i-2}$, ..., $S'(\omega)_{i-M}$. In some examples, for a $k^{th}$ reflection of the K identified reflections, the phase signal determination module 336 iterates through the M static multipath free FFT outputs and, for each static multipath free FFT output, determines a phase angle at the FFT bin associated with the $k^{th}$ reflection. Taken together, the resulting M phase angles for the $k^{th}$ reflection represent a time progression of the phase for the reflection, or the phase signal, $\phi_k'(t)$.

The phase signal for the $k^{th}$ reflection is related to the distance traveled from the transmitting antenna 104, to the moving object from which the signal reflected, and back to the receiving antenna 106 as follows:

$$\phi_k'(t) = 2\pi d_k(t)/\lambda$$

where $\lambda$ is the wavelength (e.g., 4.5 cm) of the transmitted signal, and d(t) is the traveled distance from the device to the reflector and back to the device. That is, variations in the distance traveled by the signal due to inhaling, exhaling, and heartbeats can be identified by measuring the resulting variations in the phase of the reflected signal.

2.2.3 Aperiodic Reflection Removal

In some examples, not every reflection that remains after static multipath removal necessarily corresponds to the breathing and heart rate of a subject. For example, certain reflections may correspond to limb motion such as a subject typing, moving their feet, or walking. The aperiodic signal removal module 338 distinguishes between reflections corresponding to breathing and heart rate of a subject and reflections corresponding to other types of movement. To do so, the aperiodic signal removal module 338 exploits the fact that phase signals of reflections corresponding to vital signs are periodic while phase signals of reflections corresponding to other types of movement are generally aperiodic.

To this end, the aperiodic signal removal module 338 receives the K phase signals, $\phi_1'(t), \phi_2'(t), \ldots, \phi_K'(t)$ output by the phase signal determination module 336 and processes the K phase signals to remove any of the K phase signals that are aperiodic. The output of the aperiodic signal removal module 338 includes N periodic phase signals, $\phi_1(t), \phi_2(t), \ldots, \phi_N(t)$.

In some examples, to identify the N periodic phase signals, the aperiodic signal removal module 338 processes each of the K phase signals to determine a measure of periodicity of the phase signal. If the measured periodicity of a given phase signal is above a predetermined threshold, the aperiodic signal removal module 338 includes the given phase signal in the set of N periodic phase signals, otherwise the given phase signal is not included in the set of N periodic phase signals.

In some examples, to measure the periodicity of a given phase signal, the aperiodic signal removal module 338 computes a Fourier transform (e.g., an FFT) of the phase signal and then evaluates a sharpness of the FFT of the signal. To evaluate the sharpness of the FFT of the phase signal, the aperiodic signal removal module 338 first identifies a peak value of the FFT of the phase signal. If a power associated with the identified peak value is sufficiently greater than (i.e., above the predetermined threshold) an average power at the remaining, non-peak frequencies, then the given phase signal is identified as a periodic signal. Otherwise, the given phase signal is identified as an aperiodic signal. The spectral representations of any phase signals that are identified as being periodic are included in the N periodic phase signals output by the aperiodic signal removal module 338.

In some examples, measuring the periodicity of phase signals as is described above also ensures that time intervals where a subject performs large limb movements are excluded from vital signs analysis. However, time intervals where a subject is performing small movements such as typing on a laptop computer or using a cellular telephone can still be analyzed for vital signs analysis. In particular, while such small movements may be aperiodic, they do not mask the breathing or the heart rate since their power does not overwhelm the repetitive movements due to the subject's vital signs.

The N periodic phase signals, $\phi_1(t)$, $\phi_2(t)$, ..., $\phi_N(t)$ are then output from the phase signal extraction module 122. See, for example, the N=2 outputs, $\phi_A(t)$, $\phi_B(t)$ shown in FIG. 4.

2.2.4 Example

Figure 4:
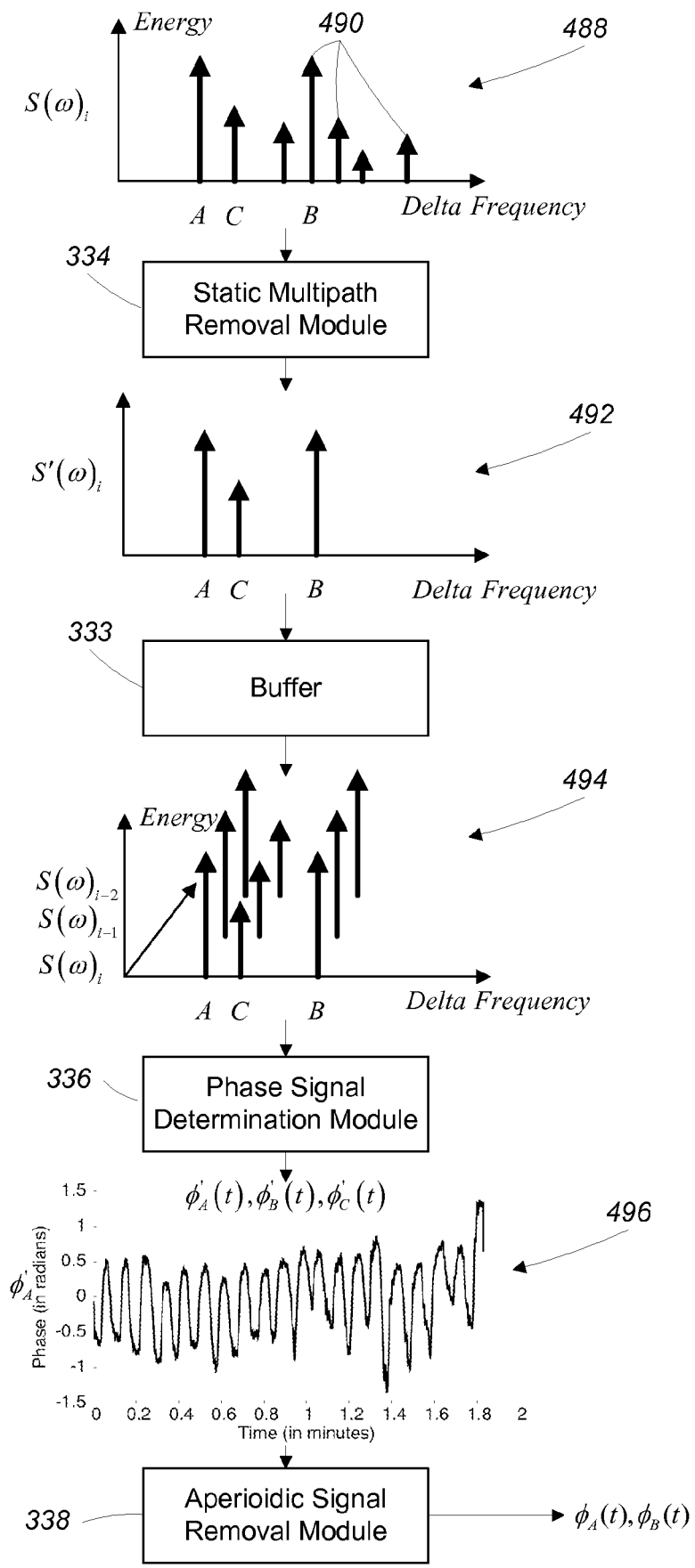
FIG. 4 is an exemplary operation of the phase signal extraction module of FIG. 3.

Referring to FIG. 4, an example of the operation of the phase signal extraction module 122 is illustrated for an exemplary FFT output, $S(\omega)_i$ 488 which includes a number of areas of concentrated energy 490 (i.e., reflections). In general, each of the areas of concentrated energy 332 corresponds to a reflection in the signal received at the receiving antenna 106. In the exemplary FFT output $S(\omega)_i$ 488, three of the areas of concentrated energy (labeled A, B, and C) correspond to reflections due to moving objects that are present in the environment. In this example, reflections A and B are due to periodic vital sign movements of subjects 102a, 102b in the environment and reflection C is due to a non-periodic movement in the environment.

The exemplary FFT output $S(\omega)_i$ is first provided to the static multipath removal module 334 along with one or more previous values of the exemplary FFT output $S(\omega)_i$ (e.g., $S(\omega)_{i-j}$). The static multipath removal module 334 uses the background subtraction technique described above to remove any reflections due to static multipath effects from the exemplary FFT output $S(\omega)_i$ resulting in the static multipath free FFT output, $S'(\omega)_i$ 492. In this example, the static multipath free FFT output, $S'(\omega)_i$ 492 includes only the reflections labeled A, B, and C which correspond to moving objects in the environment.

The static multipath free FFT output, $S'(\omega)_i$ 492 is provided to the buffer 333 which stores the static multipath free FFT output, $S'(\omega)_i$ 492 along with M−1 previous outputs of the static multipath removal module 334. The buffered static multipath free FFT outputs, $S'(\omega)_i$, $S(\omega)_{i-1}$, $S'(\omega)_{i-2}$, ..., $S'(\omega)_{i-M}$ 494 are provided to the phase signal determination module 336 which extracts a phase signal for each of the reflections in the buffered static multipath free FFT outputs, $S'(\omega)_i$, $S'(\omega)_{i-1}$, $S'(\omega)_{i-2}$, ..., $S'(\omega)_{i-M}$ 494. Since there are three reflections (i.e., A, B, and C) in the buffered static multipath free FFT outputs 494, output of the phase signal determination module 336 includes three phase signals, $\phi_A'(t)$, $\phi_B'(t)$, $\phi_C'(t)$. A plot 496 of $\phi_A'(t)$ for the example of FIG. 4 shows a substantially sinusoidal variation in the phase signal due to breathing movement. The small perturbations in the phase signal due to the heart beat movements of the subject are modulated by the substantially sinusoidal variation of the breathing movement.

The three phase signals, $\phi_A'(t)$, $\phi_B'(t)$, $\phi_C'(t)$ are provided to the aperiodic signal removal module 338 which analyzes each of the phase signals to determine whether it is periodic and then outputs only the periodic phase signals. Since, as is noted above, C is an aperiodic signal, the output of the aperiodic signal removal module 338 includes only $\phi_A(t)$, $\phi(t)$.

2.3 Phase Signal Analysis

As is illustrated in FIG. 4, a phase signal that varies due to the breathing and heart beats of a subject includes large peaks and valleys in the phase that correspond to inhalation and exhalation motions of the subject, respectively. The phase signal also includes smaller perturbations modulated on the large peaks and valleys which are due to the subject's heartbeats.

Figure 5:
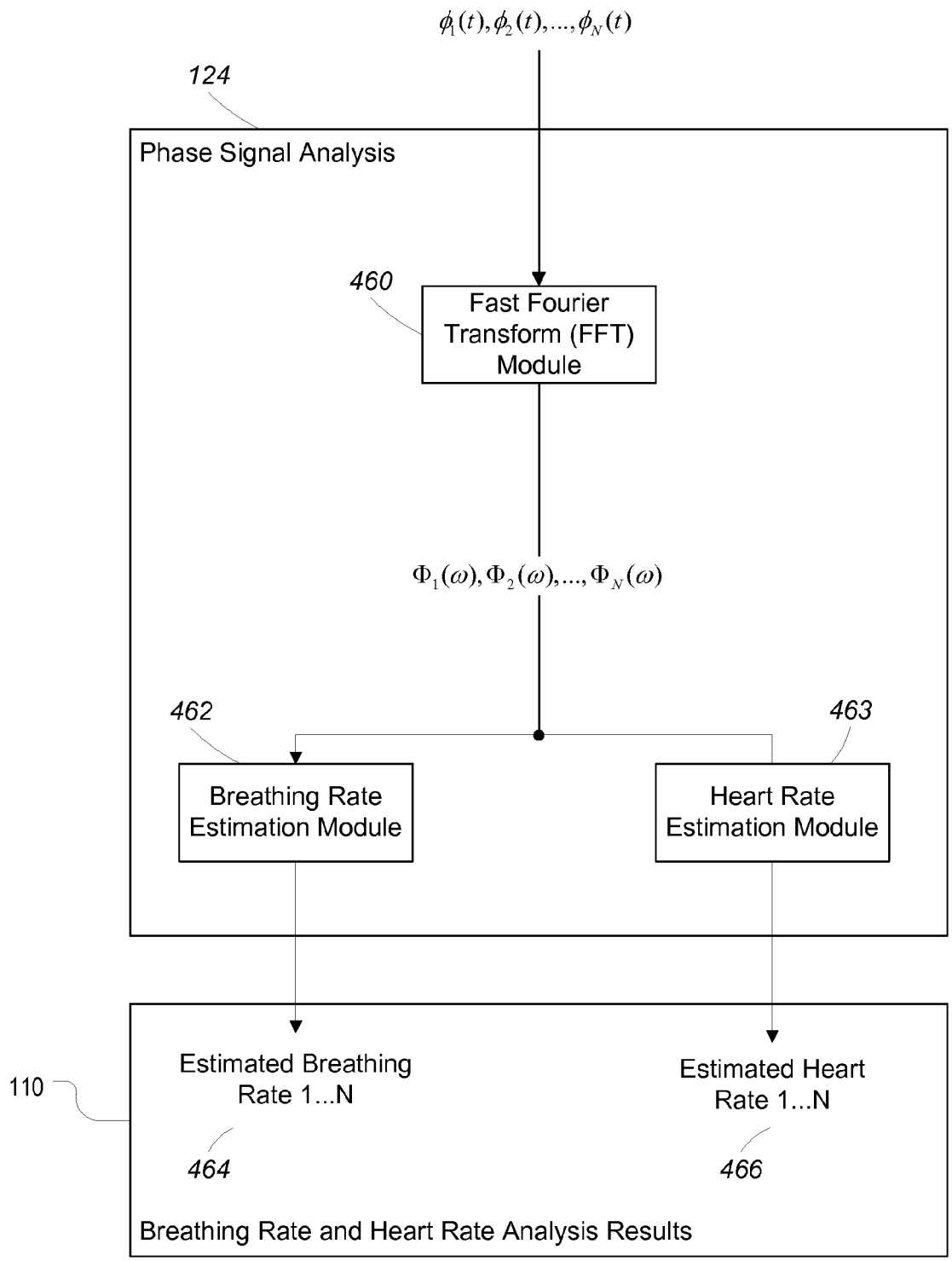
FIG. 5 is a schematic block diagram of an embodiment of a phase signal analysis module.

Referring to FIG. 5, the N periodic phase signals, $\phi_1(t)$, $\phi_2(t)$, ..., $\phi_N(t)$ are provided to the phase signal analysis module 124 (shown in FIG. 1) which processes the N periodic phase signals to determine an estimated breathing rate 464 and an estimated heart rate 466 for each of the N periodic phase signals.

In some examples, the phase signal analysis module 124 includes a Fast Fourier Transform (FFT) module 460, a breathing rate estimation module 462, and a heart rate estimation module 463. The N periodic phase signals, $\phi_1(t)$, $\phi_2(t)$, ..., $\phi_N(t)$ are first provided to the FFT module 460 which efficiently computes a discrete time Fourier transform for each of the N periodic phase signals, resulting in N FFT outputs, $\Phi_1(\omega)$, $\Phi_2(\omega)$, ..., $\Phi_N(\omega)$. In some examples, a windowing function such as a Hanning windowing function is applied to the phase signal prior to the FFT module 460 calculating the FFT of the phase signal. Application of such a windowing function reduces unwanted leakage of strong frequencies into adjacent bins in the FFT output for the phase signal.

The N FFT outputs, $\Phi_1(\omega)$, $\Phi_2(\omega)$, ..., $\Phi(\omega)$ are provided to the breathing rate estimation module 462 and to the heart rate estimation module 463.

2.3.1 Breathing Rate Estimation

Figure 6:
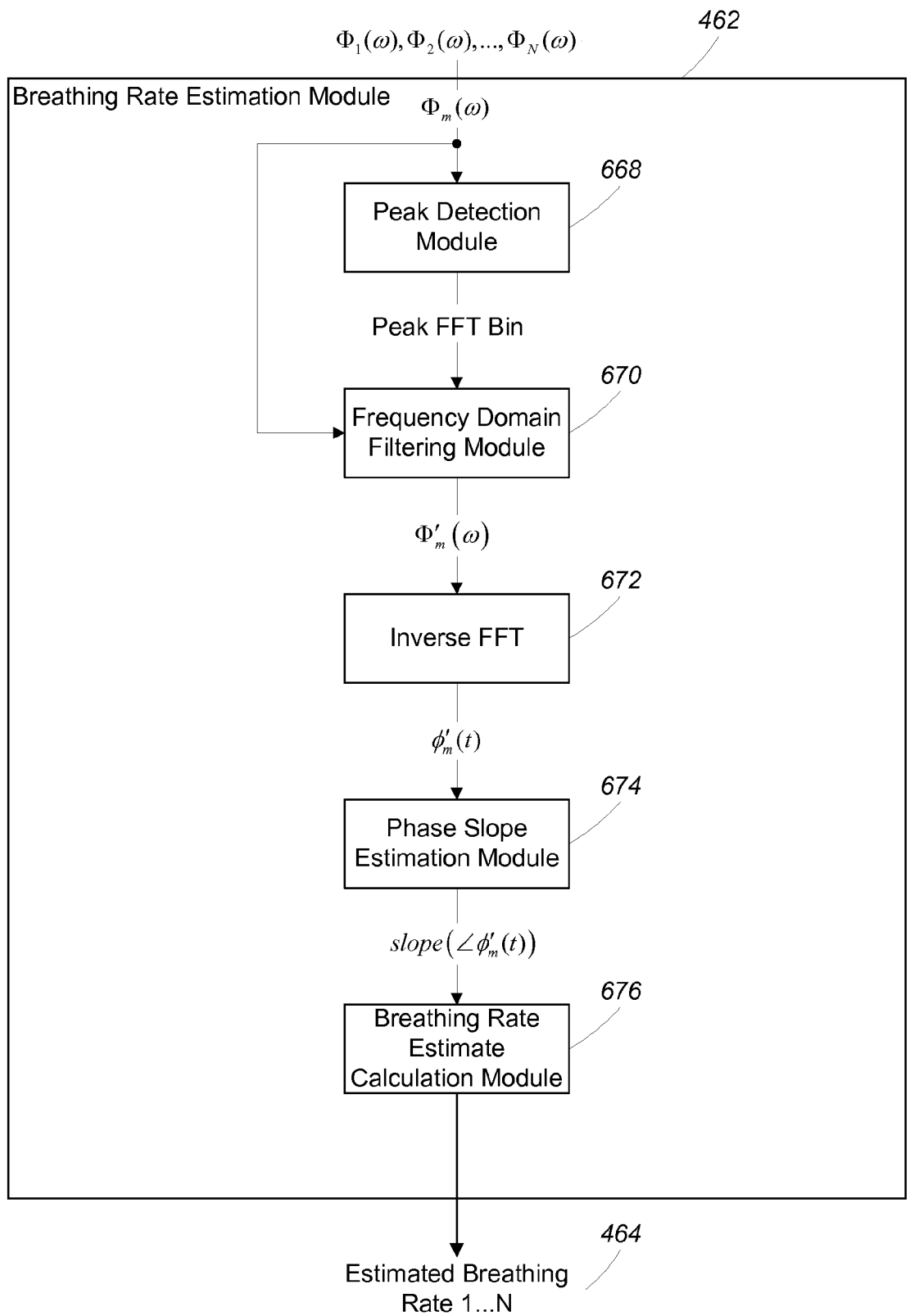
FIG. 6 is a schematic block diagram of an embodiment of a breathing rate estimation module.

Referring to FIG. 6, the breathing rate estimation module 462 receives the N FFT outputs, $\Phi_1(\omega)$, $\Phi_2(\omega)$, ..., $\Phi_N(\omega)$ and processes the N FFT outputs to determine the N estimated breathing rates 464.

In some examples, the breathing rate estimation module 462 includes a peak detection module 668, a frequency domain filtering module 670, an inverse fast Fourier transform (FFT) module 672, a phase slope estimation module, 674, and a breathing rate estimate calculation module 676.

To process a given FFT output, $\Phi_m(\omega)$, the FFT output is first provided to the peak detection module 668 which identifies an FFT bin in the FFT output, $\Phi_m(\omega)$ with a peak energy value. The identified FFT bin is associated with a frequency that is an initial, coarse estimate of the subject's breathing rate. However, simply choosing a frequency associated with the peak of the FFT output does not provide an accurate estimate of breathing rate since the frequency resolution of the FFT output is 1/window size. If the window size is, for example, 30 seconds, the resolution of the initial estimate of the subject's breathing rate is ≈0.033 Hz (i.e., 2 breaths/minute). Of course, a finer resolution is desirable.

Since a single dominant frequency exists in the FFT output, $\Phi_m(\omega)$ (i.e., at the frequency associated with the peak value identified by the peak detection module 668), a finer resolution can be obtained by performing a regression (e.g., a linear regression) on the phase of the complex time-domain signal associated with the FFT output, $\Phi_m(\omega)$. To do so, the identified peak FFT bin and the FFT output, $\Phi_m(\omega)$ are provided to the frequency domain filtering module 670 which filters out all bins of the FFT output, $\Phi_m(\omega)$ except for the identified peak FFT bin and the two FFT bins adjacent to the identified peak FFT bin. The output of the frequency domain filtering module 670 is a filtered FFT output, $\Phi'_m(\omega)$. In some examples, the filtering performed by the frequency domain filtering module 670 eliminates noise caused by extraneous and aperiodic movements.

The filtered FFT output, $\Phi'_m(\omega)$ is provided to the inverse FFT module 672 which performs an inverse FFT to obtain a complex time-domain signal, $\phi_m'(t)$ for the filtered FFT output, $\Phi'_m(\omega)$. The complex time-domain signal, $\phi_m'(t)$ is then provided to a phase slope estimation module 674 which computes the slope, of the complex time-domain signal, $\phi_m'(t)$ as:

slope($\angle\phi_m'(t)$)

The slope of the complex time-domain signal (i.e., slope ($\angle\phi_m'(t)$)) is provided to the breathing rate estimate calculation module 676 which determines a fine grained estimated breathing rate 464, in terms of breaths per minute, as:

$$\text{Estimated Breathing Rate} = \frac{60 \times \text{slope}(\angle\phi_m'(t))}{2\pi},$$

where the factor of 60 transforms the frequency from H: (i.e., 1/second) to breaths/minute.

2.3.2 Heart Rate Estimation

Figure 7:
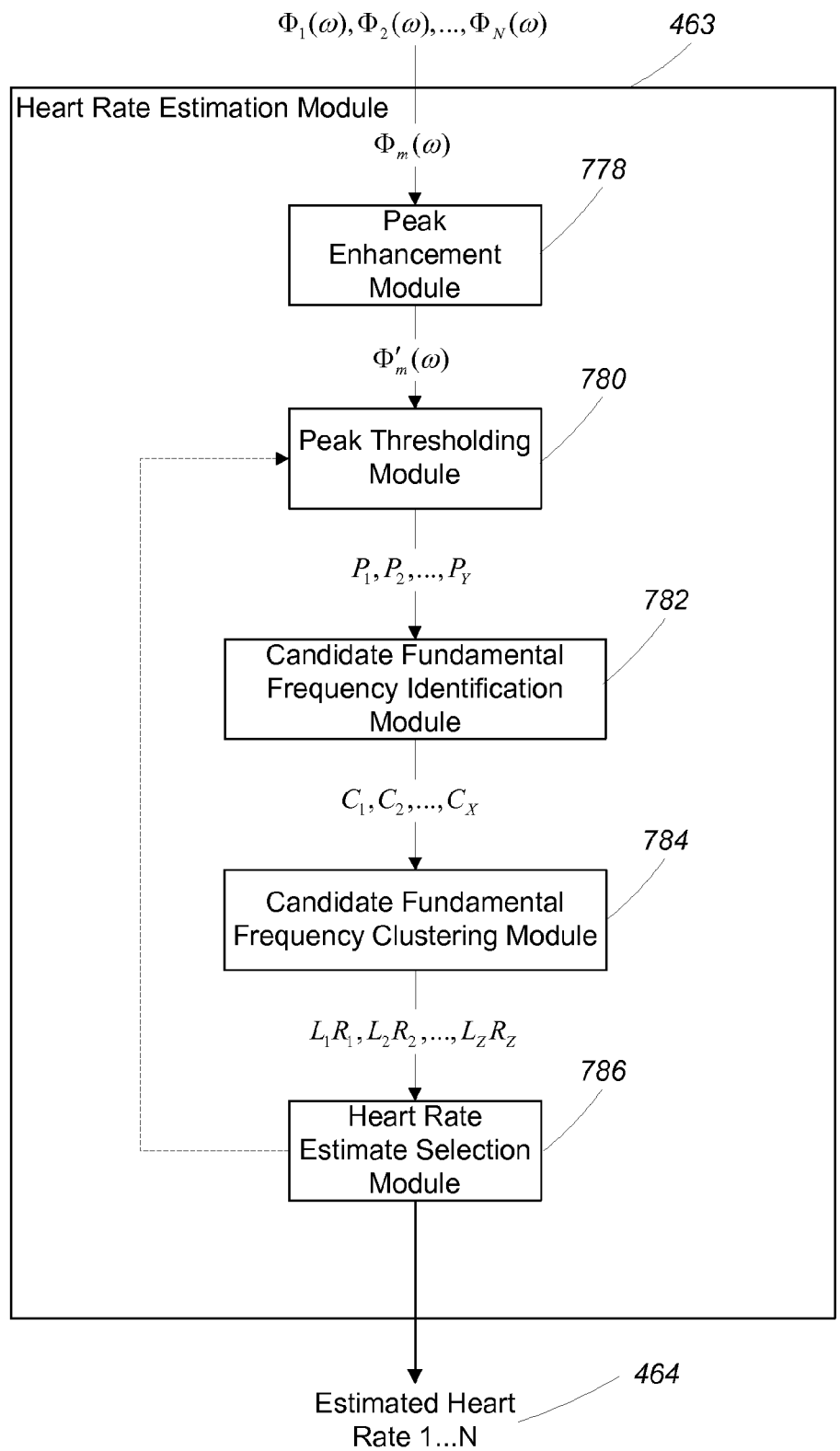
FIG. 7 is a schematic block diagram of an embodiment of a heart rate estimation module.

Referring to FIG. 7, the heart rate estimation module 463 receives the N FFT outputs, $\Phi_1(\omega), \Phi_2(\omega), \ldots, \Phi_N(\omega)$ and processes the N FFT outputs to determine the N estimated heart rates 464.

To understand the operation of the heart rate estimation module 463, it is helpful to understand that a typical breathing rate is in a range of 8-20 breaths/minute and a typical heart rate is in a range of 40-200 beats/minute. Thus, one approach to computing a heart rate estimate for a given one of the FFT outputs, $\Phi_m(\omega)$ is to simply apply a bandpass filter with a pass band of 40-200 beats/minute to the signal (or to the spectral representation of the signal). However, a challenge in doing so is that the breathing component of the phase signal associated with the FFT output, $\Phi_m(\omega)$ is typically much stronger than the heart rate component of the phase signal. Furthermore, the breathing component is not a simple sinusoid. Since the breathing component is not a simple sinusoid, it includes a fundamental component at a fundamental frequency, $f_{breathing}$ and a number of harmonics at harmonic frequencies, $2 \times f_{breathing}$, $3 \times f_{breathing}$, $4 \times f_{breathing}$, and so on.

Some of the harmonics fall into the 40-200 beats/minute frequency band of the heart rate and typically have much higher power than the frequency components related to the heart rate in the phase signal. For this reason, the harmonics of the breathing component of the phase signal can be confused with frequency components related to the heart rate in the phase signal.

To avoid this confusion, the heart rate estimation module 463 leverages the observation that the heart rate component at the fundamental frequency $f_{heartrate}$ also has harmonics (i.e., at $2 \times f_{heartrate}$, $3 \times f_{heartrate}$, $4 \times f_{heartrate}$, and so on) and that the stronger, low order harmonics of the heart rate component are collocated in frequency ranges with the weaker, high order harmonics of the breathing rate component (since the power of very subsequent harmonic is lower than the previous). Any harmonics present at frequencies above the expected frequency band for the heart rate (e.g., 40-200 beats/minute) with significant power are assumed to be harmonics of the heart rate component and can be used, as is described in detail below, to determine the fundamental frequency of the heart rate component.

For example, for a breathing rate of 15 breaths/minute, the 4th harmonic of the breathing component in the phase signal (which still has significant power) is at 60 breaths/minute and might be confused with the heart rate's fundamental component (e.g., for a heart rate of 75 beats/minute). However, the first harmonic of the heart rate component in the phase signal (i.e., at 150 beats/minute) is near the 9th harmonic of the breathing component which is very low power (since it is a high order harmonic). Hence, the heart rate harmonic (i.e., at 150 beats/minute) can be used to determine the heart rate.

However, another issue arises in that 150 beats/minute is itself a possible human heart rate. For this reason, the heart rate estimation module 463 determines whether the heart rate is 75 beats/minute (i.e., 150 beats/minute is the first harmonic of the heart rate component), if the heart rate is 150 beats/minute (i.e., 150 beats/minutes is the fundamental frequency of the heart rate component), or even if the heart rate is 50 beats/minute (i.e., 150 beats/minute is the third harmonic of the heart rate component).

To do so, the heart rate estimation module 463 also takes into account higher order (e.g., third, fourth, fifth) harmonics of the heart rate component. For example, the heart rate estimation module 463 identifies peaks in frequency bands of the phase signal that include high order harmonics of the heart rate component and uses the identified peaks to determine the heart rate.

To this end, the heart rate estimation module 463 includes a peak enhancement module 778, a peak thresholding module 780, a candidate fundamental frequency identification module 782, a candidate fundamental frequency clustering module 784, and a heart rate estimate selection module 786.

To process a given FFT output, $\Phi_m(\omega)$, the FFT output is first provided to the peak enhancement module 778 which enhances any peaks present in the power spectrum of the FFT output, $\Phi_m(\omega)$ in comparison to any noise present in the FFT bins surrounding the peaks. In some examples, the peak enhancement module 778 replaces the power in each FFT bin of the FFT output, $\Phi_m(\omega)$ with a value representing the signal-to-noise ratio (SNR) of the bin with respect to its neighboring FFT bins. For example, the value of each FFT bin in the FFT output, $\Phi_m(\omega)$ is replaced as follows:

$$\text{value[FFT\_bin]} = \frac{\text{value[FFT\_bin]}^2}{\text{average(value[adjacentFFT\_bins])}^2}$$

where adjacentFFT_bins is a range of bins (e.g., 10, 20, 50 bins) on each side of a bin of interest, FFT_bin.

The output of the peak enhancement module 778 is a peak enhanced FFT output, $\Phi_m'(\omega)$. The peak enhanced FFT output, $\Phi_m'(\omega)$ is provided to the peak thresholding module 780 which processes the peak enhanced FFT output to identify peaks, $P_1, P_2, \ldots, P_Y$ in the peak enhanced FFT output that are located in a frequency range above the expected fundamental frequency range of the heart rate component (e.g., above 200 beats/minute) and that exceed a predefined SNR threshold. See, for example, $P_1, P_2, \ldots, P_5$ in FIG. 8. Any peaks that are identified by the peak thresholding module 780 are associated with a frequency which is a candidate for the heart rate component fundamental frequency.

The identified peaks, $P_1, P_2, \ldots, P_Y$ are provided to the candidate fundamental frequency identification module 782 which, for each of the identified peaks, if the frequency associated with the peak falls within an integer multiple of the 40 to 200 beats/minute frequency range for the heart rate component, divides the frequency associated with the peak by the integer multiple and adds the result of the division as a candidate for the heart rate component fundamental frequency. For example, for an exemplary peak associated with a frequency of 220 beats/minute, the frequency falls within the frequency range of [2*40 to 2*200], [3*40 to 3*200], and [4*40 to 4*200]. As a result, 110 beats/minute (i.e., 220 beats/minute/2), 73.3 beats/minute (i.e., 220 beats/minute/3), and 55 beats/minute (i.e., 220 beats/minute/4) are added as candidates for the heart rate component fundamental frequency. The output of the candidate fundamental frequency identification module 782 is a set of X candidate fundamental frequencies for the heart rate component, $C_1, C_2, \ldots, C_X$ the set including the identified peaks and all candidates determined by the candidate fundamental frequency identification module 782

The set of X candidate fundamental frequencies, $C_1, C_2, \ldots, C_X$ is provided to the candidate fundamental frequency selection module 784 which sorts the set of candidate fundamental frequencies by frequency. A window (e.g., a rectangular window with a width of 0.8*X) is then slid along the sorted set of candidate fundamental frequencies. For each position of the window as it slides along the sorted set of candidate fundamental frequencies, a number of candidate fundamental frequencies (sometimes referred to as a ich sorts the set of candidate fundamental frequea radius of the frequencies in the cluster is computed as:

$$\text{radius} = f_{max} - f_{min}$$

where $f_{max}$ is the candidate fundamental frequency with the highest frequency in the cluster and $f_{min}$ is the candidate fundamental frequency with the lowest frequency in the cluster. In some examples, the radius is an indication of how concentrated a set of candidate fundamental frequencies in the cluster are. In general, a set of candidate fundamental frequencies in a cluster with a low radius is considered to be better than a set of candidate fundamental frequencies in a cluster with a high radius.

In some examples, each cluster and its associated radius, $L_1R_1, L_2R_2, \ldots, L_ZR_Z$ is passed to the heart rate estimate selection module 786 which processes the clusters and their associated radii to determine the estimated heart rate for the $m^{th}$ phase signal. The heart rate estimate selection module 786 selects the cluster with the lowest radius and chooses the median frequency in the cluster as the estimated heart rate 464. In some examples, if two or more clusters have the same lowest radius, the heart rate estimate selection module 786 selects the cluster of the two or more clusters with the highest average frequency since the clusters with lower average frequencies are associated with sub-harmonics of the heart rate fundamental frequency.

In some examples, the heart rate estimate selection module 786 computes a confidence ratio for the selected cluster as a ratio between the radius of the selected cluster and the radius of a next best cluster (i.e., a cluster with a radius closest to the radius of the selected cluster. The heart rate estimate selection 786 stores the estimated heart rate and its confidence ratio for later use. Then the heart rate estimation module then 463 lowers the signal to noise ratio threshold used by the peak thresholding module 780 and re-processes the peak enhanced FFT output, $\Phi_m'(\omega)$ to determine another estimated heart rate and confidence ratio. This process repeats until a predefined minimum signal to noise ratio is reached or until a predefined confidence ratio is reached.

Once the predefined minimum signal to noise ratio or the predefined confidence ratio is reached, the estimated heart rate with the highest confidence ratio is selected as the estimated heart rate for the FFT output, $\Phi_m(\omega)$. In some examples, the estimated heart rate 464 is output from the heart rate estimation module 463.

In other examples, the selected estimated heart rate is treated as a coarse estimate of the fundamental frequency of the heart rate and further processing is used to determine a fine-grained estimate from the coarse estimate.

In particular, as was the case above with the breathing rate, a finer resolution estimate of the fundamental frequency of the heart rate can be obtained by performing a regression (e.g., a linear regression) on the phase of the complex time-domain signal associated with the FFT output, $\Phi_m(\omega)$. To do so, the FFT bin associated with the identified coarse fundamental frequency estimate and the FFT output, $\Phi_m(\omega)$ are provided to the frequency domain filtering module (not shown) which filters out all bins of the FFT output, $\Phi_m(\omega)$ except for the identified FFT bin and the two FFT bins adjacent to the identified FFT bin. The output of the frequency domain filtering module is a filtered FFT output, $\Phi_m(\omega)$. In some examples, the filtering performed by the frequency domain filtering module eliminates noise caused by extraneous and aperiodic movements.

The filtered FFT output, $\Phi_m'(\omega)$ is provided to an inverse FFT module (not shown) which performs an inverse FFT to obtain a complex time-domain signal, $\phi_m'(t)$ for the filtered FFT output, $\phi_m'(\omega)$. The complex time-domain signal, $\phi_m'(t)$ is then provided to a phase slope estimation module (not shown) which computes the slope, of the complex time-domain signal, $\phi_m'(t)$ as:

$$\text{slope}(\angle \phi_m'(t))$$

The slope of the complex time-domain signal (i.e., slope $(\angle \phi_m'(t))$) is used to determine a fine grained estimated heart rate, in terms of beats per minute, as:

$$\text{Estimated Heart Rate} = \frac{60 \times \text{slope}(\angle \phi_m'(t))}{2\pi},$$

where the factor of 60 transforms the frequency from H: (i.e., 1/second) to beats/minute.

2.3.2.1 Example of Heart Rate Estimation

Figure 8:
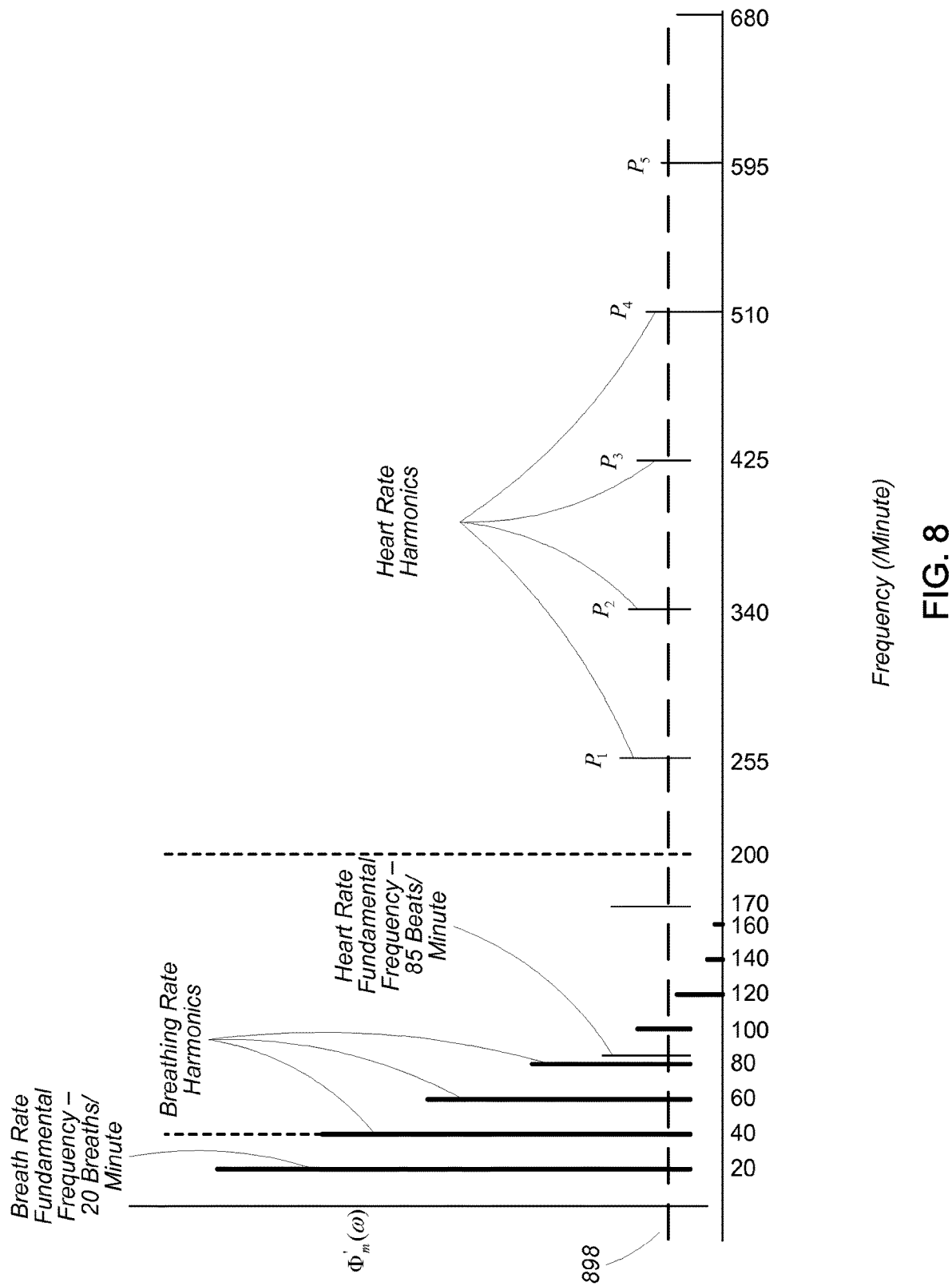
FIG. 8 is a spectral representation of an exemplary phase signal including components related to a subject's breathing and components related to a subject's heart beat.

Referring to FIG. 8, a plot of a peak enhanced FFT output, $\Phi_m'(\omega)$ for an exemplary FFT output $\Phi_m(\omega)$ includes peaks at a fundamental breathing rate frequency of 20 breaths/minute and at a number of harmonic breathing rate frequencies at integer multiples of 20 breaths/minute (i.e., 40 breaths/minute, 60 breaths/minute, 80 breaths/minute, and so on). The plot also includes peaks at a fundamental heart rate frequency of 85 beats/minute and at a number of harmonic frequencies at integer multiples of 85 beats/minute (i.e., 170 beats/minute, 225 beats/minute, 340 beats/minute, and so on).

The peak enhanced FFT output, $\Phi_m'(\omega)$ is provided to the peak thresholding module 780 of FIG. 7 which applies a threshold 898 to the peak enhanced FFT output to identify peaks in the peak enhanced FFT output that are located in a frequency range above the expected fundamental frequency range of the heart rate component (i.e., above 200 beats/minute) and that exceed the predefined SNR threshold 898. In this example, there are five peaks, $P_1, P_2, \ldots, P_5$ that are located in a frequency range above the expected fundamental frequency range of the heart rate component and that exceed the predefined SNR threshold 898. $P_1$ is located at a frequency of 255 beats/minute. $P_2$ is located at a frequency of 340 beats/minute. $P_3$ is located at a frequency of 425 beats/minute. $P_4$ is located at a frequency of 510 beats/minute. $P_5$ is located at a frequency of 595 beats/minute.

The five identified peaks, $P_1, P_2, \ldots, P_5$ are provided to the candidate fundamental frequency identification module 784 which, for each of the identified peaks, if the frequency associated with the peak falls within an integer multiple of the 40 to 200 beats/minute frequency range for the heart rate component, divides the frequency associated with the peak by the integer multiple and adds the result of the division as a candidate for the heart rate component fundamental frequency. In this example, for $P_1$ which is located at 255 beats/minute, the candidate frequencies 127.5, 85, 63.75, 51, 42.5 are added as candidates for the heart rate component fundamental frequency. For $P_2$ which is located at a frequency of 340 beats/minute, the candidate frequencies 170, 113.3, 85, 68, 56.7, 48.6, 42.5 are added as candidates for the heart rate component fundamental frequency. For $P_3$ which is located at a frequency of 425 beats/minute, the candidate frequencies 141.7, 106.25, 85, 70.8, 60.7, 53.1, 47.2, 42.5 are added as candidates for the heart rate component fundamental frequency. For $P_4$ which is located at a frequency of 510 beats/minute, the candidate frequencies 170, 127.5, 102, 85, 72.9, 63.8, 56.7, 51, 46.3, 42.5 are added as candidates for the heart rate component fundamental frequency. For $P_5$ which is located at a frequency of 595 beats/minute, the candidate frequencies 198.3, 148.8, 119, 99.2, 85, 74.4, 66.1, 59.5, 54.1, 49.6, 45.8, 42.5 are added as candidates for the heart rate component fundamental frequency.

Figure 9:
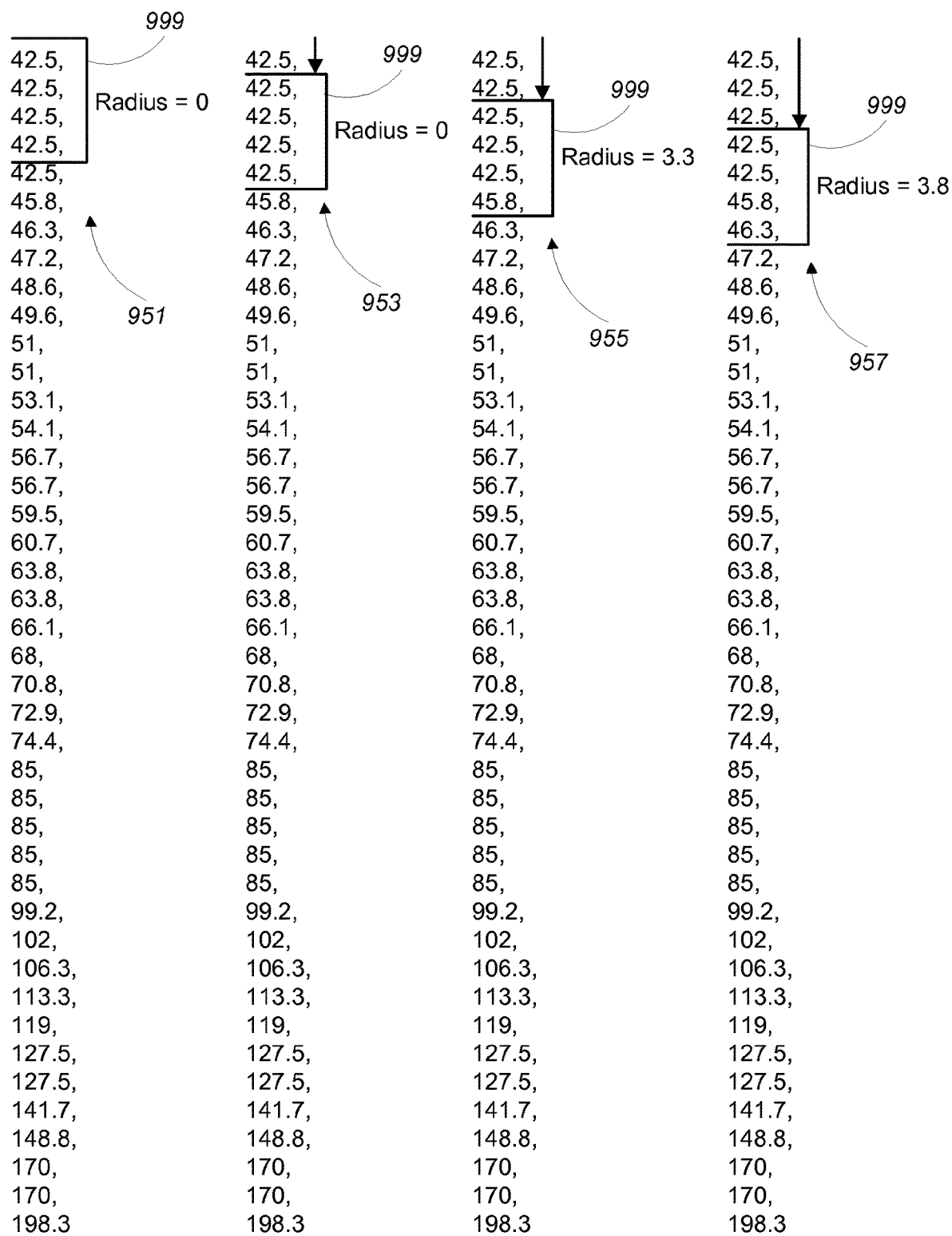
FIG. 9 illustrates an exemplary operation of candidate fundamental frequency clustering module.

Referring to FIG. 9, the set of candidate for the heart rate component fundamental frequencies determined $C_1, C_2, \ldots, C_X$ is provided to the candidate fundamental frequency clustering module 784 which sorts the set of candidate fundamental frequencies by frequency. A window (i.e., a rectangular window with a width of 4 candidates) is then slid along the sorted set of candidate fundamental frequencies. For each position of the window, a radius of the frequencies in the in the window (i.e., a cluster) is computed as:

$$\text{radius} = f_{max} - f_{min}$$

where $f_1a$ is the candidate fundamental frequency with the highest frequency in the cluster and $f_{min}$ is the candidate fundamental frequency with the lowest frequency in the cluster. For example, when the window 999 in a first position 951, the radius of the cluster is equal to zero. When the window 999 is in a second position 953, the radius of the cluster is equal to 0. When the window 999 is in a third position 955, the radius of the cluster is equal to 3.3. When the window 999 is in a fourth position 957, the radius of the cluster is equal to 3.8.

Figure 10:
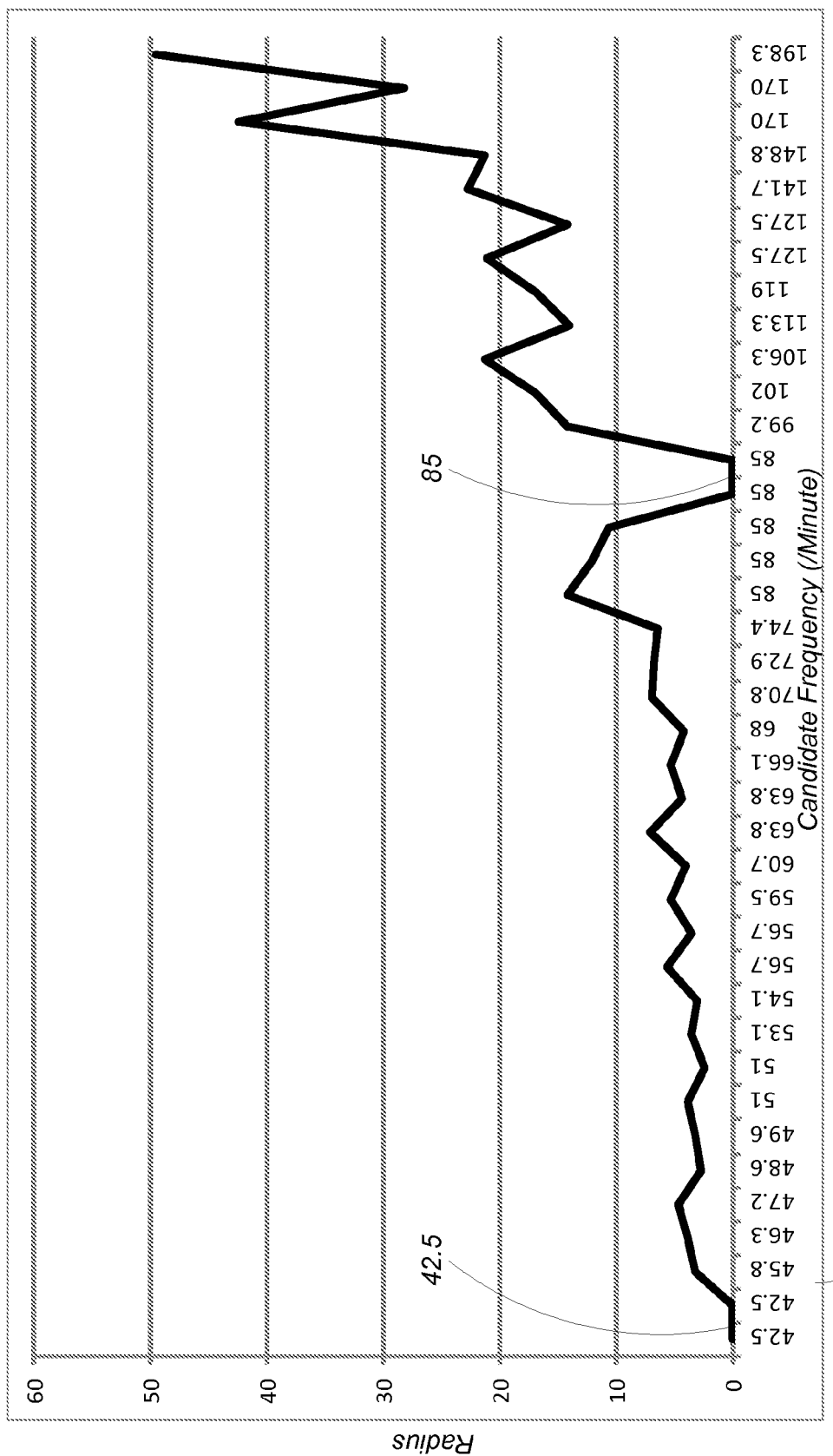
FIG. 10 is a plot of a radius vs. candidate fundamental frequencies.

Referring to FIG. 10, a plot 1061 of the radius as the window 999 slides along the sorted set of candidate fundamental frequencies includes two frequencies where the radius is at a minimum: 42.5 beats/minute and 85 beats/minute.

The clusters and the associated radii determined by the candidate fundamental frequency clustering module 784 are provided to the heart rate estimate selection module 786 which selects the cluster with the lowest radius as being the cluster that includes the fundamental frequency for the heart rate. In this case, since two or more clusters have the same lowest radius (i.e., 0), the heart rate estimate selection module 786 selects the cluster of the two or more clusters with the highest average frequency since the clusters with the lowest average frequency are associated with sub-harmonics of the heart rate fundamental frequency. The median frequency of the selected cluster (i.e., 85 beats/minute) is selected as the heart rate fundamental frequency and is output as the estimated heart rate 464 for $\Phi_m(\omega)$ As is noted above, in some examples, the heart rate estimate selection module 786 calculates a confidence ratio for the selected cluster as a ratio between the radius of the selected cluster and the radius of a next best cluster. The heart rate estimate selection module 786 stores the estimated heart rate and its confidence ratio for later use. Then the heart rate estimation module then 463 lowers the signal to noise ratio threshold used by the peak thresholding module 780 and re-processes the peak enhanced FFT output, $\Phi_m'(\omega)$ to determine another estimated heart rate and confidence ratio. This process repeats until a predefined minimum signal to noise ratio is reached or until a predefined confidence ratio is reached.

3 Alternatives

In some examples, rather than analyzing the harmonics of the heart beat component of the phase signal, the heart rate estimation module uses a filter based approach to determine an estimate for the heart rate. For example, the heart rate estimation module filters the phase signal using a bandpass filter with a pass band in a frequency range (e.g., 40 to 200 beats/minute) where the heart beat component of the phase signal is assumed to exist. An FFT of the filtered phase signal is calculated and a peak in the FFT output is identified. Note that, in some examples, the absolute maximum of the FFT output is not chosen as the identified peak since it is due to leakage from the breathing component of the phase signal. An inverse FFT of the signal in the FFT bin corresponding to the identified peak and the two FFT bins adjacent to the FFT bin corresponding to the identified peak is then calculated. A phase regression is then used to determine the heart rate estimate (as is done for the breathing rate estimate).

While the above description describes how a single antenna pair is used to it is noted that a number of antenna pairs can be used to improve the performance of the system. For example, signals received at a number of receive antennas can be combined in various ways to determine an exact location of reflecting bodies and can be combined to obtain a cleaner, less noisy phase signal for a reflecting body. In some implementations, a separate phase signal is obtained from each pair of antennas and spectral peaks are identified for each pair of antenna, with the peaks of several pairs being combined to estimate the fundamental frequency, for example, all pairs voting together. In other implementations, different pairs of antennas are processed separately to determine separate fundamental frequency estimates that are combined.

4 Implementations

Systems that implement the techniques described above can be implemented in software, in firmware, in digital electronic circuitry, or in computer hardware, or in combinations of them. The system can include a computer program product tangibly embodied in a machine-readable storage device for execution by a programmable processor, and method steps can be performed by a programmable processor executing a program of instructions to perform functions by operating on input data and generating output. The system can be implemented in one or more computer programs that are executable on a programmable system including at least one programmable processor coupled to receive data and instructions from, and to transmit data and instructions to, a data storage system, at least one input device, and at least one output device. Each computer program can be implemented in a high-level procedural or object-oriented programming language, or in assembly or machine language if desired; and in any case, the language can be a compiled or interpreted language. Suitable processors include, by way of example, both general and special purpose microprocessors. Generally, a processor will receive instructions and data from a read-only memory and/or a random access memory. Generally, a computer will include one or more mass storage devices for storing data recordings; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM disks. Any of the foregoing can be supplemented by, or incorporated in, ASICs (application-specific integrated circuits).

It is to be understood that the foregoing description is intended to illustrate and not to limit the scope of the invention, which is defined by the scope of the appended claims. Other embodiments are within the scope of the following claims.

What is claimed is:

1. A method for monitoring one or more periodic motions of one or more subjects using signal reflections from the subjects, the method comprising:
    emitting a transmitted signal comprising repetitions of a transmitted signal pattern from a transmitting antenna;
    receiving, at one or more receiving antennas, a received signal comprising a combination of a plurality of reflections of the transmitted signal, at least some reflections of the plurality of reflections of the transmitted signal being associated with the one or more subjects;
    processing the received signal to form time successive patterns of the reflections of the transmitted signal from the one or more subjects, including forming a subset of the plurality of reflections including removing at least some extraneous reflections of the plurality of reflections according to reflection distance;
    processing the time successive patterns of reflections to form one or more phase signals including, for each reflection of the subset of the plurality of reflections, forming a phase signal representing a variation over time of a phase angle for the reflection of the transmitted signal in the received signal; and
    processing each phase signal of a subset of the one or more phase signals to determine an estimate of a fundamental frequency of each periodic motion of the one or more periodic motions.

2. The method of claim 1 wherein forming the subset of the reflections includes, for each reflection of the plurality of reflections of the transmitted signal, determining whether the reflection is a static multipath reflection, excluding the reflection from the subset of the reflections if the reflection is a static multipath reflection, and including the reflection in the subset of the reflections if the reflection is not a static multipath reflection.

3. The method of claim 2 wherein determining whether the reflection is a static multipath reflection includes using a time differencing approach.

4. The method of claim 1 further comprising determining the subset of the one or more phase signals including processing each of the one or more phase signals to determine a measure of periodicity of the phase signal and including the phase signal in the subset of the one or more phase signals if the measure of periodicity of the phase signal exceeds a predetermined threshold.

5. The method of claim 1 wherein determining the estimate of the fundamental frequency of each periodic motion of the one or more periodic motions includes, for each periodic motion of the one or more periodic motions, determining a preliminary estimate of the fundamental frequency for the periodic motion and determining the estimate of the fundamental frequency for the periodic motion based on the preliminary estimate and a regression of the phase signal.

6. The method of claim 1 wherein the one or more periodic motions include periodic motions associated with one or more vital signs of a subject.

7. The method of claim 1 wherein the one or more periodic motions includes a periodic motion associated with heart beats of a subject.

8. The method of claim 1 wherein the one or more periodic motions includes a periodic motion associated with a subject breathing.

9. The method of claim 1 wherein the one or more periodic motions includes a periodic motion associated with an interfering movement of a subject.

10. The method of claim 1 wherein the one more periodic motions includes a periodic motion associated with a subject breathing and further includes a periodic motion associated with heart beats of the subject.

11. The method of claim 1 wherein processing each phase signal of the subset of the one or more phase signals to determine an estimate of a fundamental frequency of each periodic motion of the one or more periodic motions includes identifying a plurality of spectral peaks in a frequency domain representation of the phase signal, at least some of the spectral peaks being located at harmonic frequencies of the estimate of the fundamental frequency, and determining the estimate of the fundamental frequency from the identified one or more spectral peaks.

12. The method of claim 11 wherein determining the estimate of the fundamental frequency from the identified one or more spectral peaks includes processing the one or more spectral peaks to determine a plurality of candidate fundamental frequencies for the periodic motion.

13. The method of claim 12 wherein processing the one or more spectral peaks to determine the plurality of candidate fundamental frequencies for the periodic motion includes,
for each spectral peak, determining one or more factors of a frequency associated with the spectral peak that are in an expected frequency range of the fundamental frequency for the periodic motion, and
including the determined one or more factors in the plurality of candidate fundamental frequencies for the periodic motion.

14. The method of claim 12 further comprising processing the plurality of candidate fundamental frequencies to determine a preliminary estimate of the fundamental frequency for the periodic motion.

15. The method of claim 14 further comprising determining the estimate of the fundamental frequency based on the preliminary estimate of the fundamental frequency and a regression of the phase signal.

16. The method of claim 15 further comprising
filtering the phase signal to form a filtered version of the phase signal, including retaining frequency components at the preliminary estimate of the fundamental frequency and frequency components adjacent to the preliminary estimate of the fundamental frequency in the filtered version of the phase signal, and excluding substantially all other frequencies from the filtered version of the phase signal; and
determining the estimate of the fundamental frequency of the periodic motion based on a regression of the filtered version of the phase signal.

17. The method of claim 16 wherein determining the estimate of the fundamental frequency of the periodic motion based on a regression of the filtered version of the phase signal includes determining a slope of a phase angle of the filtered version of the phase signal.

18. The method of claim 14 wherein processing the plurality of candidate fundamental frequencies to determine the preliminary estimate of the fundamental frequency includes applying a voting algorithm to the plurality of candidate fundamental frequencies.

19. The method of claim 11 wherein each phase signal of the subset of the one or more phase signals includes a first plurality of spectral peaks related to a periodic motion due to heart beats of the subject and a second plurality of spectral peaks related to a periodic motion due to the subject breathing.

20. The method of claim 11 wherein identifying the plurality of spectral peaks in the frequency domain representation of the phase signal includes applying a normalization algorithm to distinguish the spectral peaks from a noise floor of the frequency domain representation.

21. The method of claim 1 wherein processing the phase signal of the subset of one or more phase signals to determine the estimate of the fundamental frequency of each periodic motion of the one or more periodic motions includes iteratively processing the phase signal.

22. The method of claim 1 wherein at least some of the subjects are humans.

23. The method of claim 1 wherein the subset of the one or more phase signals includes a plurality of phase signals.

24. The method of claim 1 wherein, for each phase signal of the subset of the one or more phase signals, determining the estimate of the fundamental frequency for the periodic motion includes
determining a preliminary estimate of the fundamental frequency of the periodic motion; and
determining the estimate of the fundamental frequency of the periodic motion based on the preliminary estimate of the fundamental frequency of the periodic motion and a regression of the phase signal.

25. The method of claim 24 wherein
determining the preliminary estimate of the fundamental frequency of the periodic motion includes identifying a frequency associated with a largest peak in a spectral representation of the phase signal; and
determining the estimate of the fundamental frequency of the periodic motion includes
filtering the phase signal to form a filtered version of the phase signal, including retaining frequency components at the preliminary estimate and frequency components adjacent to the preliminary estimate in the filtered version of the phase signal, and excluding substantially all other frequencies from the filtered version of the phase signal, and
determining the estimate of the fundamental frequency of the periodic motion based on a regression of the filtered version of the phase signal.

26. The method of claim 25 wherein determining the estimate of the fundamental frequency of the periodic motion based on a regression of the filtered version of the phase signal includes determining a slope of a phase angle of the filtered version of the phase signal.

27. The method of claim 1 wherein one or more of the extraneous reflections correspond to one or more objects in the environment.

28. The method of claim 27 wherein the one or more objects are moving.

29. The method of claim 28 wherein the one or more objects are periodically moving.

30. The method of claim 29 wherein the one or more objects includes a fan.

31. The method of claim 27 wherein the one or more objects are static.

32. The method of claim 28 wherein the one or more objects are vibrating.

33. The method of claim 32 wherein the vibration of the one or more objects is periodic.

34. The method of claim 1 wherein removing extraneous reflections of the plurality of reflections according to reflection distance enables extraction of periodic movements of a plurality of subjects concurrently.

35. The method of claim 1 wherein removing extraneous reflections of the plurality of reflections according to reflection distance enables eliminating reflections form one or more different body parts of a human.

36. The method of claim 35 wherein the one or more different body parts includes a limb.

37. The method of claim 1 wherein removing extraneous reflections of the plurality of reflections according to reflection distance enables eliminating reflections from one or more different objects on a human's body.

38. The method of claim 37 wherein the one or more different objects includes wearable objects including watches, cellular telephones, and jewelry.

39. The method of claim 1 wherein, after being processed, the received signals from various human body parts are combined to obtain an estimate of the fundamental frequencies of the one or more periodic motions with increased accuracy.

40. A computer-implemented system for monitoring one or more periodic motions of one or more subjects using signal reflections from the subjects, the system comprising a processor programmed to perform all the steps of any one of claims 1 to 39.

41. The system of claim 40 further comprising a transmitter for emitting the transmitted signal and a receiver for receiving the received.

42. Software stored on a non-transitory computer-readable medium comprising instructions for causing a processor to perform all the steps of any one of claims 1 to 39.

* * * * *